United States Patent
Lam et al.

(10) Patent No.: US 10,130,259 B2
(45) Date of Patent: Nov. 20, 2018

(54) SYSTEMS FOR OPTICAL IMAGING OF BIOLOGICAL TISSUES

(71) Applicant: BRITISH COLUMBIA CANCER AGENCY BRANCH, Vancouver (CA)

(72) Inventors: Stephen Lam, Vancouver (CA); Pierre Lane, North Vancouver (CA); Anthony Lee, Vancouver (CA); Hamid Pahlevaninezhad, North Vancouver (CA); Calum Macaulay, Vancouver (CA)

(73) Assignee: British Columbia Cancer Agency Branch, Vancouver (CA)

( * ) Notice: Subject to any disclaimer, the term of this patent is extended or adjusted under 35 U.S.C. 154(b) by 281 days.

(21) Appl. No.: 15/117,145

(22) PCT Filed: Feb. 5, 2015

(86) PCT No.: PCT/CA2015/050085
§ 371 (c)(1),
(2) Date: Aug. 5, 2016

(87) PCT Pub. No.: WO2015/117241
PCT Pub. Date: Aug. 13, 2015

(65) Prior Publication Data
US 2017/0196459 A1 Jul. 13, 2017

Related U.S. Application Data

(60) Provisional application No. 61/936,003, filed on Feb. 5, 2014, provisional application No. 62/004,602, filed on May 29, 2014.

(51) Int. Cl.
*G01B 9/02* (2006.01)
*A61B 5/00* (2006.01)
(Continued)

(52) U.S. Cl.
CPC .......... *A61B 5/0066* (2013.01); *A61B 5/0071* (2013.01); *A61B 5/7235* (2013.01);
(Continued)

(58) Field of Classification Search
CPC .................. G01B 9/02091; G01B 9/02049
See application file for complete search history.

(56) References Cited

U.S. PATENT DOCUMENTS 5,202,745 A 4/1993 Sorin et al.
5,459,570 A 10/1995 Swanson et al.
(Continued)

FOREIGN PATENT DOCUMENTS

EP 2278267 A2 1/2011
EP 1804638 B1 12/2012
(Continued)

OTHER PUBLICATIONS

Al-Qaisi, M. K. et al., "Polarization-sensitive optical coherence tomography based on polarization-maintaining fibers and frequency multiplexing", Opt. Express 16(17), 13032-13041 (2008).
(Continued)

*Primary Examiner* — Jonathan Hansen
(74) *Attorney, Agent, or Firm* — Oyen Wiggs Green & Mutala LLP

(57) ABSTRACT

A fiber-based polarization sensitive optical coherence tomography (PS-OCT) system uses a new polarization diversity detection (PDD) scheme and requires no active polarization modulating components. Retardation of the sample can be determined from amplitudes of arbitrarily-oriented x- and y-components of the reflected light. A hybrid custom 50/50 coupler with single-mode fiber inputs and polarization maintaining (PM) fiber outputs combines light from sample and reference arms of an interferometer. Another embodiment provides a system adapted to provide
(Continued)

co-registered autofluorescence-optical coherence tomography (AF-OCT) imaging. AF excitation light is introduced and collected AF light is extracted at a fiber optic rotary joint (FORJ) equipped with an embedded dichroic mirror. A probe tip that uses a clad fiber to supply light to a focusing element provides enhanced OCT and AF performance.

23 Claims, 16 Drawing Sheets

(51) Int. Cl.
    *G01N 21/64*     (2006.01)
    *G02B 6/27*     (2006.01)
    *G02B 6/36*     (2006.01)
    *G02B 6/028*     (2006.01)

(52) U.S. Cl.
    CPC ..... *G01B 9/02004* (2013.01); *G01B 9/02091* (2013.01); *G01N 21/6456* (2013.01); *G02B 6/0288* (2013.01); *G02B 6/2706* (2013.01); *G02B 6/2746* (2013.01); *G02B 6/3604* (2013.01); *G01B 2290/70* (2013.01); *G01N 2021/6484* (2013.01); *G01N 2201/061* (2013.01)

(56) References Cited

U.S. PATENT DOCUMENTS

| | | |
|---|---|---|
| 5,748,598 A | 5/1998 | Swanson et al. |
| 5,784,352 A | 7/1998 | Swanson et al. |
| 6,134,003 A | 10/2000 | Tearney et al. |
| 6,445,939 B1 | 9/2002 | Swanson et al. |
| 6,501,551 B1 | 12/2002 | Tearney et al. |
| 6,564,087 B1 | 5/2003 | Pitris et al. |
| 6,564,089 B2 | 5/2003 | Izatt et al. |
| 6,615,072 B1 | 9/2003 | Izatt et al. |
| 6,831,781 B2 | 12/2004 | Tearney et al. |
| 6,904,199 B2 | 6/2005 | Zuluaga |
| 7,102,756 B2 | 9/2006 | Izatt et al. |
| 7,261,687 B2 | 8/2007 | Yang |
| 7,362,444 B2 | 4/2008 | Izatt et al. |
| 7,362,500 B2 | 4/2008 | Ye et al. |
| 7,364,543 B2 | 4/2008 | Yang et al. |
| 7,366,376 B2 | 4/2008 | Shishkov et al. |
| 7,382,949 B2 | 6/2008 | Bouma et al. |
| 7,447,408 B2 | 11/2008 | Bouma et al. |
| 7,576,865 B2 | 8/2009 | Chen et al. |
| 7,705,992 B2 | 4/2010 | Hatori et al. |
| 7,809,225 B2 | 10/2010 | Bouma et al. |
| 7,809,226 B2 | 10/2010 | Bouma et al. |
| 7,813,609 B2 | 10/2010 | Petersen et al. |
| 7,920,271 B2 * | 4/2011 | Vakoc ............... A61B 3/1225 356/479 |
| 7,925,133 B2 | 4/2011 | Bouma et al. |
| 7,929,148 B2 | 4/2011 | Kemp |
| 7,952,718 B2 | 5/2011 | Li et al. |
| RE43,875 E | 12/2012 | Shishkov et al. |
| 8,363,225 B2 | 1/2013 | Rolland et al. |
| 8,369,669 B2 | 2/2013 | Bouma et al. |
| 8,503,844 B2 | 8/2013 | Petersen et al. |
| 8,676,013 B2 | 3/2014 | Bouma et al. |
| 8,712,506 B2 | 4/2014 | Courtney et al. |
| 8,792,757 B2 | 7/2014 | Boudoux et al. |
| 8,903,475 B2 | 12/2014 | Brennan et al. |
| 2003/0072069 A1 | 4/2003 | Li et al. |
| 2003/0179992 A1 | 9/2003 | Robilliard et al. |
| 2006/0158655 A1 | 7/2006 | Everett et al. |
| 2008/0097224 A1 | 4/2008 | Murphy et al. |
| 2008/0252900 A1 | 10/2008 | Hatori |
| 2013/0023760 A1 | 1/2013 | Liu et al. |
| 2013/0331689 A1 | 12/2013 | Le et al. |
| 2014/0275986 A1 | 9/2014 | Vertikov |
| 2014/0276108 A1 | 9/2014 | Vertikov |
| 2014/0309527 A1 | 10/2014 | Namati et al. |
| 2017/0074638 A1* | 3/2017 | Fukuhara ............... A61B 3/102 |
| 2018/0000341 A1* | 1/2018 | Tomatsu ............... A61B 3/102 |

FOREIGN PATENT DOCUMENTS

| | | |
|---|---|---|
| EP | 2659852 A2 | 11/2013 |
| EP | 2677272 A1 | 12/2013 |
| EP | 2412298 B1 | 11/2014 |
| WO | 9732182 A1 | 9/1997 |
| WO | 2008154460 A1 | 12/2008 |
| WO | 2013168149 A1 | 11/2013 |

OTHER PUBLICATIONS

Bao, H. et al., "Nonlinear endomicroscopy using a double-clad fiber coupler", Opt. Lett. 35(7), 995-997 (2010).
Barton, J. K. et al., "Dual modality instrument for simultaneous optical coherence tomography imaging and fluorescence spectroscopy", J. Biomed. Opt. 9(3), 618-623 (2004).
Baumann, B. et al., "Swept-source/Fourier domain polarization sensitive optical coherence tomography with a passive polarization delay unit", Opt. Express 20(9), 10218-10230 (2012).
Bonesi, M. et al., "High-speed polarization sensitive optical coherence tomography scan engine based on Fourier domain mode locked laser", Biomed. Opt. Express 3(11), 2987-3000 (2012).
Bonnema, G. T. et al., "A concentric three element radial scanning optical coherence tomography endoscope", J. Biophoton. 2(6-7), 353-356 (2009).
Bouma, B. E. et al., "Fourier-domain optical coherence tomography: recent advances toward clinical utility", Curr. Opin. Biotechnol. 20(1), 111-118 (2009).
Chen, Y. et al., "Integrated optical coherence tomography (OCT) and fluorescence laminar optical tomography (FLOT)", IEEE Journal of Selected Topics in Quantum Electronics 16(4), 755-766 (2010).
Dai, X. et al., "Simultaneous optical coherence tomography and autofluorescence microscopy with a single light source", J. Biomed. Opt. 17(8), 080502-1 to 080502-3 (2012).
Dave, D. P. et al., "Polarization-maintaining fiber-based optical low-coherence reflectometer for characterization and ranging of birefringence", Opt. Lett. 28(19), 1775-1777 (2003).
De Boer, J. F. et al., "Determination of the depth-resolved Stokes parameters of light backscattered from turbid media by use of polarization-sensitive optical coherence tomography", Opt. Lett. 24(5), 300-302 (1999).
De Boer, J. F. et al., "Imaging thermally damaged tissue by polarization sensitive optical coherence tomography", Opt. Express 3(6), 212-218 (1998).
De Boer, J. F. et al., "Two-dimensional birefringence imaging in biological tissue by polarization-sensitive optical coherence tomography", Opt. Lett. 22(12), 934-936 (1997).
Everett, M. J. et al., "Birefringence characterization of biological tissue by use of optical coherence tomography", Opt. Lett. 23(3), 228-230 (1998).
Fard, A. M. et al., "Optical coherence tomography—near infrared spectroscopy system and catheter for intravascular imaging", Opt. Express 21(25), 30849-30858 (2013).
Fujimoto, J. G. et al., "High resolution in vivo intra-arterial imaging with optical coherence tomography", Heart 82(2), 128-133 (1999).
Fujimoto, J. G. et al., "Optical biopsy and imaging using optical coherence tomography", Nat. Med. 1(9), 970-972 (1995).
Gaertner, M. et al., "Investigation of alveolar tissue deformations using OCT combined with fluorescence microscopy", Proc. SPIE 8091, Optical Coherence Tomography and Coherence Techniques V, 80911P-1 to 80911P-6 (2011).
Gotzinger, E. et al., "Polarization maintaining fiber based ultra-high resolution spectral domain polarization sensitive optical coherence tomography", Opt. Express 17(25), 22704-22717 (2009).
Hariri, L. P. et al., "Endoscopic optical coherence tomography and laser-induced fluorescence spectroscopy in a murine colon cancer model", Lasers Surg. Med. 38(4), 305-313 (2006).

(56) References Cited

OTHER PUBLICATIONS

Hee, M. R. et al., "Polarization-sensitive low-coherence reflectometer for birefringence characterization and ranging", J. Opt. Am. B 9(6), 903-908 (1992).
Hitzenberger, C. K. et al., "Measurement and imaging of birefringence and optic axis orientation by phase resolved polarization sensitive optical coherence tomography", Opt. Express 9(13), 780-790 (2001).
Huang, D., et al., "Optical Coherence Tomography", Science 254(5035), 1178-1181 (1991).
Hung, J. et al., "Autofluorescence of normal and malignant bronchial tissue", Lasers in Surgery and Medicine 11(2), 99-105 (1991).
Jiao, S. et al., "Depth-resolved two-dimensional Stokes vectors of backscattered light and Mueller matrices of biological tissue measured with optical coherence tomography", Appl. Opt. 39(34), 6318-6324 (2000).
Ju, M. J. et al., "Advanced multi-contrast Jones matrix optical coherence tomography for Doppler and polarization sensitive imaging", Opt. Express 21, 19412-19436 (2013).
Kang, J. U. et al., "Common-path optical coherence tomography for biomedical imaging sensing", J. Opt. Soc. Korea 14(1), 1-13 (2010).
Kennedy, T. C. et al., "Review of recent advances in fluorescence bronchoscopy in early localization of central airway lung cancer", Oncologist 6(3), 257-262 (2001).
Kim, K. H. et al., "Polarization-sensitive optical frequency domain imaging based on unpolarized light", Opt. Express 19(2). 552-561 (2010).
Kobayashi, M. et al.,"Polarization-independent interferometric optical-time-domain reflectometer", J. Lightwave Technol. 9(5), 623-628 (1991).
Lam, S. et al., "Localization of bronchial intraepithelial neoplastic lesions by fluorescence bronchoscopy", Chest 1133), 696-702 (1998).
Lam, S. Lam et al., "In vivo optical coherence tomography imaging of preinvasive bronchial lesions", Clin. Cancer Res. 14(7), 1078-0432 (2008).
Lee, A. M. D. et al., "In vivo lung microvasculature visualized in three dimensions using fiber-optic color Doppler optical coherence tomography", J Biomed Opt, 18(5), 050501-1 to 050501-3 (2013).
Lee, A. M. D. et al., "Fiber-optic polarization diversity detection for rotary probe optical coherence tomography", Optics Letters 39(12), 3638-3641 (2014).
Lemire-Renaud, S. et al., "Double-clad fiber coupler for endoscopy", Opt. Express 18(10), 9755-9764 (2010).
Li, X. et al., "Imaging needle for optical coherence tomography", Opt. Lett. 25(20), 1520-1522 (2000).
Li, X. et al., "Intraluminal fiber-optic Doppler imaging catheter for structural and functional optical coherence tomography", Opt. Lett. 26(23), 1906-1908 (2001).
Li, X. D. et al., "Optical coherence tomography: advanced technology for the endoscopic imaging of Barrett's esophagus", Endoscopy 32(12), 921-30 (2000).
Lu, Z. et al., "Optic axis determination by fibre-based polarization-sensitive swept-source coherence tomography", Phys. Med. Biol. 56, 1105-1122 (2011).
Liang, S. et al., "Intravascular atherosclerotic imaging with combined fluorescence and optical coherence tomography probe based on a double-clad fiber combiner," J. Biomed. Opt. 17(7), 070501-1 to 070501-3 (2012).
Liu, G. et al., "Fiber-based combined optical coherence and multiphoton endomicroscopy", J. Biomed. Opt. 16(3), 036010-1 to 036010-4 (2011).
Lorenser, B. C. et al., "Dual-modality needle probe for combined fluorescence imaging and three-dimensional optical coherence tomography", Opt. Lett. 38(3), 266-268 (2013).
Lorenser, D. et al., "Ultrathin side-viewing needle probe for optical coherence tomography", Opt. Lett. 36(19), 3894-3896 (2011).
Lu, Z. et al., "Conical scan polarization-sensitive optical coherence tomography", Biomed Opt. Express 5(3), 752-762 (2014).

Mavadia, J. et al., "An all-fiber-optic endoscopy platform for simultaneous OCT and fluorescence imaging", Biomed. Optics Express 3(11), 2851-2859 (2012).
McNichols, R. J. et al., "Development of an endoscopic fluorescence image guided OCT probe for oral cancer detection", Proc. SPIE 4254, 23-30 (2001).
Murari, K. et al., "Compensation-free, all-fiber-optic, two-photon endomicroscopy at 1.55 µm", Opt. Lett. 36(7), 1299-1301 (2011).
Myaing, M. T. et al., "Fiber-optic scanning two-photon fluorescence endoscope", Opt. Lett. 31(8), 1076-1078 (2006).
Oh, W. Y. et al., "High-speed polarization sensitive optical frequency domain imaging with frequency multiplexing", Opt. Express 16(2), 1096-1103 (2008).
Pahlevaninezhad, H.et al., "Multimodal tissue imaging: using coregistered optical tomography data to estimate tissue autofluorescence intensity change due to scattering and absorption by neoplastic epithelial cells", J. Biomed. Opt. 18(10), 106007 (2013).
Pan, Y. T. et al., "Enhancing early bladder cancer detection with fluorescence-guided endoscopic optical coherence tomography", Opt. Lett. 28(24), 2485-2487 (2003).
Park, B. H. et al., "In vivo burn depth determination by high-speed fiber-based polarization sensitive optical coherence tomography", J. Biomed. Opt. 6(4), 474-479 (2001).
Park, B. H. et al., "Real-time multi-functional optical coherence tomography", Opt. Express 11(7), 782-793 (2003).
Park, B. H. et al., "Jones matrix analysis for a polarization-sensitive optical coherence tomography system using fiber-optic components", Opt. Lett. 29(21), 2512-2514 (2004).
Park, J. et al., "A dual-modality optical coherence tomography and fluorescence lifetime imaging microscopy system for simultaneous morphological and biochemical tissue characterization", Biomed. Opt. Express 1(1), 2010.
Pierce, M. C. et al., "Effects of sample arm motion in endoscopic polarization-sensitive optical coherence tomography," Opt. Express 13(15), 5739-5749 (2005).
Pierce, M. C. et al., "Simultaneous intensity, birefringence, and flow measurements with high-speed fiber-based optical coherence tomography", Opt. Lett. 27(17), 1534-1536 (2002).
Qu, J. Y. et al., "Excitation-and-collection geometry insensitive fluorescence imaging of tissue-simulating turbid media", Appl. Opt. 39(19), 3344-3356 (2000).
Rollins, M. et al., "Optimal interferometer designs for optical coherence tomography", Opt. Lett. 24(21), 1484-1486 (1999).
Ryu, S. Y. et al., "Combined system of optical coherence tomography and fluorescence spectroscopy based on double-cladding fiber", Opt. Lett. 33(20), 2347-2349 (2008).
Saxer, C. E. et al., "High-speed fiber-based polarization-sensitive optical coherence tomography of in vivo human skin", Opt. Lett. 25(18), 1355-1357 (2000).
Tang, S. et al., "Combined multiphoton microscopy and optical coherence tomography using a 12-fs broadband source", J. Biomed. Opt. 11(2), 020502 (2006).
Tang, S. et al., "Design and implementation of fiber-based multiphoton endoscopy with microelectromechaninical systems scanning", J Biomed. Opt. 14(3), 034005 (2009).
Tang, S. et al., "Multiscale multimodal imaging with multiphoton microscopy and optical coherence tomography", Opt. Lett. 36(24), 4800-4802 (2011).
Tearney, G. J. et al., "In vivo endoscopic optical biopsy with optical coherence tomography", Science 276(5321), 2037-2039 (1997).
Tearney, G. J. et al., "Scanning single-mode fiber optic catheter-endoscope for optical coherence tomography", Opt. Lett. 21(7), 543-545 (1996).
Tsuboi, M. et al., "Optical coherence tomography in the diagnosis of bronchial lesions", Lung Cancer 49(3), 387-394 (2005).
Tumlinson, A. R. et al., "Miniature endoscope for simultaneous optical-coherence tomography and laser-induced fluorescence measurement", Appl. Opt. 43(1), 113-121 (2004).
Tumlinson, A. R. et al., "Endoscope-tip interferometer for ultrahigh resolution frequency domain optical coherence tomography in mouse colon", Opt. Express 14(5), 1878-1887 (2006).

(56) References Cited

OTHER PUBLICATIONS

Venmans, B. J. et al., "Early detection of pre-invasive lesions in high risk patients. A comparison of conventional fiber optic and fluorescence bronchoscopy", J. Bronchoscopy 5(4), 280-283 (1998).

Villiger, M. et al., "Spectral binning for mitigation of polarization mode dispersion artifacts in catheter-based optical frequency domain imaging", Opt. Express 21, 16353 (2013).

Wall, R. A. et al., "Novel focused OCT-LIF endoscope", Biomed. Opt. Express 2(3), 421-430 (2011).

Wang, L. et al., "Optical probe based on double-clad optical fiber for fluorescence spectroscopy", Opt. Express 15(26), 17681-17689 (2007).

Wang, Z. et al., "Depth-encoded all-fiber swept source polarization sensitive OCT", Biomed. Opt Express 5, 2931 (2014).

Winkler, A. M. et al., "In vivo, dual-modality OCT/LIF imaging using a novel VEGF receptor-targeted NIR fluorescent probe in the AOM-treated mouse model", Mol. Imaging Biol. 13(6), 1173-1182 (2011).

Yamanari, M. et al., "Polarization-sensitive swept source optical coherence tomography with continuous source polarization modulation", Opt. Express 16(8), 5892-5906 (2008).

Yao, G. et al., "Two-dimensional depth-resolved Mueller matrix characterization of biological tissue by optical coherence tomography", Opt. Lett. 24(8), 537-539 (1999).

Yelin, B. E et al., "Double-clad fiber for endoscopy," Opt. Lett. 29(20), 2408-2410 (2004).

Yuan, S. et al., "Co-registered optical coherence tomography and fluorescence molecular imaging for simultaneous morphological and molecular imaging", Phys. Med. Biol. 55(1), 191-206 (2010).

Yuan, S. et al., "Three-dimensional coregistered optical coherence tomography and line-scanning fluorescence laminar optical tomography," Opt. Lett. 34(11), 1615-1617 (2009).

Yun, S. H. et al., "High-speed wavelength-swept semiconductor laser with a polygon-scanner-based wavelength filter", Opt. Lett. 28(20), 1981-1983 (2003).

Yun, S. H. et al., "Comprehensive volumetric optical microscopy in vivo", Nat. Med. 12, 1429 (2006).

Zhang, E. Z. et al., "Numerical compensation of system polarization mode dispersion in polarization-sensitive optical coherence tomography", Opt. Express 21, 1163 (2013).

\* cited by examiner

SYSTEMS FOR OPTICAL IMAGING OF BIOLOGICAL TISSUES

CROSS-REFERENCE TO RELATED APPLICATIONS

This application claims priority from U.S. Application No. 61/936,003 filed 5 Feb. 2014 and entitled POLARIZATION DIVERSITY DETECTION FOR OPTICAL COHERENCE TOMOGRAPHY and U.S. Application No. 62/004,602 filed 29 May 2014 and entitled A HIGH-EFFICIENCY, FIBER-BASED CO-REGISTERED AUTOFLUORESCENCE-OPTICAL COHERENCE TOMOGRAPHY IMAGING SYSTEM. For purposes of the United States, this application claims the benefit under 35 U.S.C. § 119 of U.S. Application No. 61/936,003 filed 5 Feb. 2014 and U.S. Application No. 62/004,602 filed 29 May 2014, both of which are hereby incorporated herein by reference for all purposes.

FIELD

This invention relates to imaging of biological tissues and most particularly to imaging using optical coherence tomography (OCT) and/or fluorescence (which may be autofluorescence in some embodiments). Some embodiments provide co-registered OCT and autofluorescence (AF) imaging.

BACKGROUND

Histology is currently the most accurate way to study tissue morphology even though the shape and the size of tissue components do not necessarily remain intact during the fixation, embedding, and sectioning processes involved in histology. Histology has the disadvantage that it requires tissue samples to be removed from patients in biopsy procedures.

Optical methods for studying tissue morphology in vivo have the advantage over histology that biopsies are not required. Optical coherence tomography (OCT) is an interferometric technique for obtaining images depicting subsurface tissue morphology. OCT images can have axial resolution of less than 10 μm and may image tissues to depths of more than 1 mm. OCT can be used to study high-risk tissue sites without performing unnecessary biopsies and tissue removal [8]. Micro-invasive carcinoma can be distinguished from normal bronchial epithelium using epithelium thickness information measured by OCT [9]. However, compared to histology, current OCT techniques do not provide as detailed structural information about certain tissue components such as smooth muscle and different types of collagen.

A. Polarization-Sensitive OCT

Interrogating tissue by polarized light, polarization-sensitive OCT (PS-OCT) can provide additional information about birefringence properties of tissue. PS-OCT may provide better differentiation between selected tissue components as compared to polarization-insensitive OCT imaging.

Early PS-OCT systems were implemented by Michelson interferometers in free space using bulk optical components [4-11]. Controlling the polarization state of light and obtaining stable polarization states are much more feasible in free-space interferometers than in fiber-based interferometers since the polarization state of light does not change as it propagates in free space. In contrast, single mode fibers do not preserve the polarization of light due to the fiber birefringence associated with any deviation from fiber circular symmetry. Despite this disadvantage, fiber-based interferometers are much more tolerant to alignment and handling issues than free-space interferometers, offering the possibility of more robust systems for clinical use. In addition, the difficulties associated with implementing circulators with bulk optical components restrict the implementation of free space interferometers to cases where the signal to noise ratio (SNR) is high.

C. E. Saxer, et al., [12] used a fiber-based PS-OCT system to image burned tissue in vivo to determine the burn depth [13]. Saxter et al. calculated the retardation of a sample even though the exact incident polarization states on the sample were unknown.

M. C. Pierce, et al., [14] and B. H. Park, et al., [15, 16] showed that tissue birefringence and optics axis can be determined by data from alternating the polarization states of incident beam for successive A-lines at two polarization states perpendicular in a Poincaré sphere. However, this approach requires oversampling and restricted lateral scanning speed since the two-state polarization interrogation needs to be carried out at (nearly) the same location [17, 18]. Also, in an endoscopic PS-OCT system based on this method, sample arm motions affected the measurements [19].

Frequency multiplexing can be used to simultaneously measure the reflectance of two input polarization states, overcoming issues associated with sample arm motion or birefringence changes of the optical probe due to the probe bending or rotation [17, 20]. This method increases system cost and requires elaborate synchronization.

B. Baumann, et al., [18] reported an alternative approach to multiplexed PS-OCT using a passive polarization delay unit. This system was capable of operating at faster A-line scanning rates and did not require complex synchronization.

Polarization-maintaining (PM) fibers have been used to build PS-OCT systems [21-25]. However, due to the large birefringence of PM fibers, the lengths of the reference and sample arms' paths had to be exactly equal or additional numerical processing is required [23, 24].

Rotary and rotary-pullback fiber optic probes are widely used scanning mechanisms for generating 2-dimensional and 3-dimensional OCT images, respectively, of cylindrically symmetric structures. These probes are commonly made using single mode (SM) optical fiber and driven from the proximal end using rotary motors. Flexible torque-transmitting elements such as speedometer cables are used to transmit the rotary motion to the distal imaging tip. As the spinning SM fiber is continuously flexing and in motion, the polarization state of the light being emitted from the tip is constantly varying. Since the reference arm in a Mach-Zehnder interferometer does not share a common path with the sample arm the varying polarization state introduced by the rotating probe in combination with the fixed polarization state of light in the non-moving reference arm tends to create imaging artifacts.

One approach to mitigating the polarization effects of a rotating fiber optic sample arm is to use a common path probe where a partial reflection at the distal tip of the probe serves as the reference arm [36, 37]. However, being a Michelson type of OCT interferometer, this type of probe has less sensitivity relative to Mach-Zehnder interferometers [38]. An alternative approach to compensate for polarization effects in rotating probes is to use a polarization-diversity detection (PDD) scheme [39, 40]. In this scheme, polarization beam splitters are used to separate an interference signal into orthogonal polarization states. The reference beam power is equalized between the two polarization states and an image may be made from the square root of the sum of the squares of the intensities of the polarization states.

PDD schemes have been realized in the literature using free-space optics configurations [20, 41]. However, this type of setup is costly, difficult to miniaturize, and cumbersome since it involves the alignment of multiple beamsplitters and collimators. A fiber-based PDD OCT system is commercially available (PSOCT-1300, Thorlabs Inc.). However, balancing this system requires iterative adjustment of up to four polarization controllers and does not necessarily converge rapidly to an acceptable solution.

Autofluorescence (AF) bronchoscopy has proven to be more sensitive (up to 6 times) for detecting intraepithelial neoplastic lesions than white-light bronchoscopy [42-45]. AF imaging can provide valuable information about biochemical properties of tissue. AF imaging used in combination with OCT imaging (AF-OCT imaging) can provide biochemical information co-localized with structural information. The complementary nature of these two types of information makes AF-OCT imaging interesting for diagnostic applications. For instance, AF-OCT imaging can be used to study how disease processes change the structural as well as biochemical properties of airway tissue.

An AF-OCT system can be used to estimate AF loss due to epithelial scattering and absorption since the AF signal measured at the epithelial surface includes epithelial scattering and absorption effects [48]. Correcting AF intensity to remove the effects of absorption and scattering introduced by varying epithelial thickness determined by OCT can identify the contribution of submucosa fluorophores to the AF signal. OCT can measure epithelium thickness directly and determine which portion of the AF signal loss may be attributed to additional epithelial scattering.

OCT systems are typically designed to operate in the near infrared wavelength range where there is a good balance between tissue penetration and resolution. However, AF imaging systems are usually designed with visible or UV light sources to access biological chromophores. Optical components capable of operating in these two very different wavelength ranges are required to combine the two modalities. Also, endoscopic imaging of cylindrically symmetric structures such as airways typically uses rotary fiber optic probes. Combining AF and OCT is particularly challenging when imaging endoscopically via fiber optic probes. Several articles have been published on methods for combining OCT and AF imaging.

A combined AF-OCT imaging system can be obtained by combining two separate imaging systems either in free space using bulk optical components and dichroic mirrors [49-54], or by using a probe with separate adjacent fibers for the two modalities [55-61]. The former approach is unsuitable for imaging hard-to-reach places such as airways. The latter approach compromises the co-registration of the two modalities.

Other reported approaches used single Ti-Sapphire broadband femtosecond (fs) laser sources for both spectral domain OCT and multiphoton excited fluorescence imaging systems [63-70]. Using double-clad fibers (DCF) can provide a common path for the two modalities, ensuring co-registration [71-78]. Also, owing to the large inner cladding, DCFs have proven to be effective for the collection of AF emission photons [76,77].

There remains a need for robust practical and cost-effective systems for performing OCT and/or fluorescence-based imaging. There is a particular need for such systems capable of imaging narrow airways in the lung. A practical and cost-effective imaging system that combines OCT imaging (optionally PS-OCT) and fluorescence imaging (optionally AF imaging) would be highly beneficial for use in cancer screening and treatment as well as other medical applications. Such a system could be applied to guide biopsies and/or to make biopsies unnecessary in some circumstances.

SUMMARY

This invention has a number of aspects. These aspects may be applied individually or used in combination with one another. These aspects include, without limitation:
Apparatus and methods for polarization-sensitive OCT;
Apparatus and methods for co-registered AF and OCT imaging;
Apparatus and methods for fluorescence imaging;
Fiber optic polarisation diversity light detection apparatus (which may be used for polarization sensitive OCT and/or non-polarization-sensitive OCT);
Hybrid optical couplers (light combiners) for use in interferometer systems (including Mach-Zehnder interferometers);
Fiber optic rotary joints (FORT) for use in AF-OCT imaging systems;
Fiber optic probes for use in fluorescence imaging (which may optionally be autofluorescence imaging) and/or OCT imaging; and
Methods for OCT, AF and combined OCT-AF imaging.
Methods for imaging vasculature, particularly in narrow passages such as airways of the lung.

One example aspect provides apparatus for optical coherence tomography. The apparatus comprises a reference arm, a sample arm, and a light splitter connected to direct a first portion of light from a light source into the reference arm by way of a first non-polarization-maintaining optical fiber path and a second portion of light from the light source into the sample arm by way of a second non-polarization-maintaining optical fiber path. A light combiner is connected to receive light from the reference arm by way of a third non-polarization-maintaining optical fiber path and to receive light from the sample arm by way of a non-polarization-maintaining optical fiber path. The light combiner is configured to allow interference of the light received from the source and reference arms. The light combiner has first and second outputs respectively connected to first and second polarizing beam splitters by first and second polarization maintaining optical fiber paths. The first and second polarizing beam splitters each have first and second outputs. The first outputs of the first and second polarizing beam splitters are connected by polarization maintaining optical fibers to deliver light having a first state of polarization to a first light detector. The second outputs of the first and second polarizing beam splitters are connected by polarization maintaining optical fibers to deliver light having a second state of polarization distinct from the first state of polarization to a second light detector. In some embodiments the light combiner comprises a 50/50 optical coupler.

Another example aspect provides a probe useful for optical imaging. The probe comprises a dual clad optical fiber optically coupled to a probe tip. The probe tip comprises a focusing element, arranged to direct light onto a deflecting element and a clad optical fiber coupling light from the dual clad optical fiber to the focusing element. In some embodiments the clad optical fiber comprises a step-index multimode fiber. The focusing element may comprise, for example, a graded index optical fiber> In some such embodiments a length of the section of clad fiber satisfies:

$$L_{MMF} \times \frac{2\lambda_{OCT}}{\pi w_{OCT} n_{OCT}} < D_{GRIN},$$

where $w_{OCT}$, and $n_{OCT}$ are respectively the half of the mode field diameter of the core of the dual clad fiber and refractive index of a core of the clad fiber at the wavelength $\lambda_{OCT}$ of the light source and $D_{GRIN}$ is a core diameter of the graded index optical fiber. In some embodiments a diameter $D_{MMF}$ of the core of the clad fiber is given by:

$$D_{MMF} > L_{MMF} \times \frac{2\lambda_{OCT}}{\pi w_{OCT} n_{OCT}}.$$

In some embodiments, diameters of a core of the graded index optical fiber, a core of the clad fiber and an inner cladding of the dual clad fiber are all the same to within 5%.

A probe according to the invention may optionally be applied in combination with: a fiber-based interferometer wherein the probe is in a sample arm of the interferometer; and/or a fluorescence imaging system wherein the probe passes fluorescence excitation light to a sample (e.g. a tissue in vivo) and collects light from fluorescence in the sample.

Another aspect of the invention provides a method for imaging vasculature in narrow passages such as airways. The method comprises scanning a luminal surface of a passage with a probe as described herein while directing fluorescence excitation light through the dual clad fiber and monitoring collected fluorescence light passed back to a photodetector through the dual clad fiber. In some embodiments, scanning comprises rotating the probe while pulling the probe back along the passage. In some embodiments the collected fluorescence light is autofluorescence light. In some embodiments an image resolution of 60 µm or better is achieved.

Another aspect of the invention provides an interferometer comprising a hybrid custom 50/50 coupler with single-mode fiber inputs and polarization maintaining (PM) fiber outputs which combines reflections from the sample and reference arms. Since the PM fibers are located after the reflections from the two arms are combined the lengths of the PM fibers do not need to be accurately matched. Embodiments of this aspect can provide simple, low cost solution with relaxed alignment and handling issues compared to the PDD and PS-OCT systems with bulk optic polarization-sensitive detection.

Further aspects and example embodiments are illustrated in the accompanying drawings and/or described in the following description. A person skilled in the art will realize that other embodiments of the invention are possible and that the details of the invention can be modified in a number of respects, all without departing from the inventive concepts described herein. Thus, the following drawings, descriptions and examples are to be regarded as illustrative in nature and not restrictive.

BRIEF DESCRIPTION OF THE DRAWINGS

The accompanying drawings illustrate non-limiting example embodiments of the invention.

FIG. 2A shows OCT signal amplitudes for two detection channels. FIG. 2B shows retardation. FIG. 2C shows change in retardation with axial depth and change in retardation with the orientation of the quarter-wave plate.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Example OCT System Architecture

Figures 1, 1A:
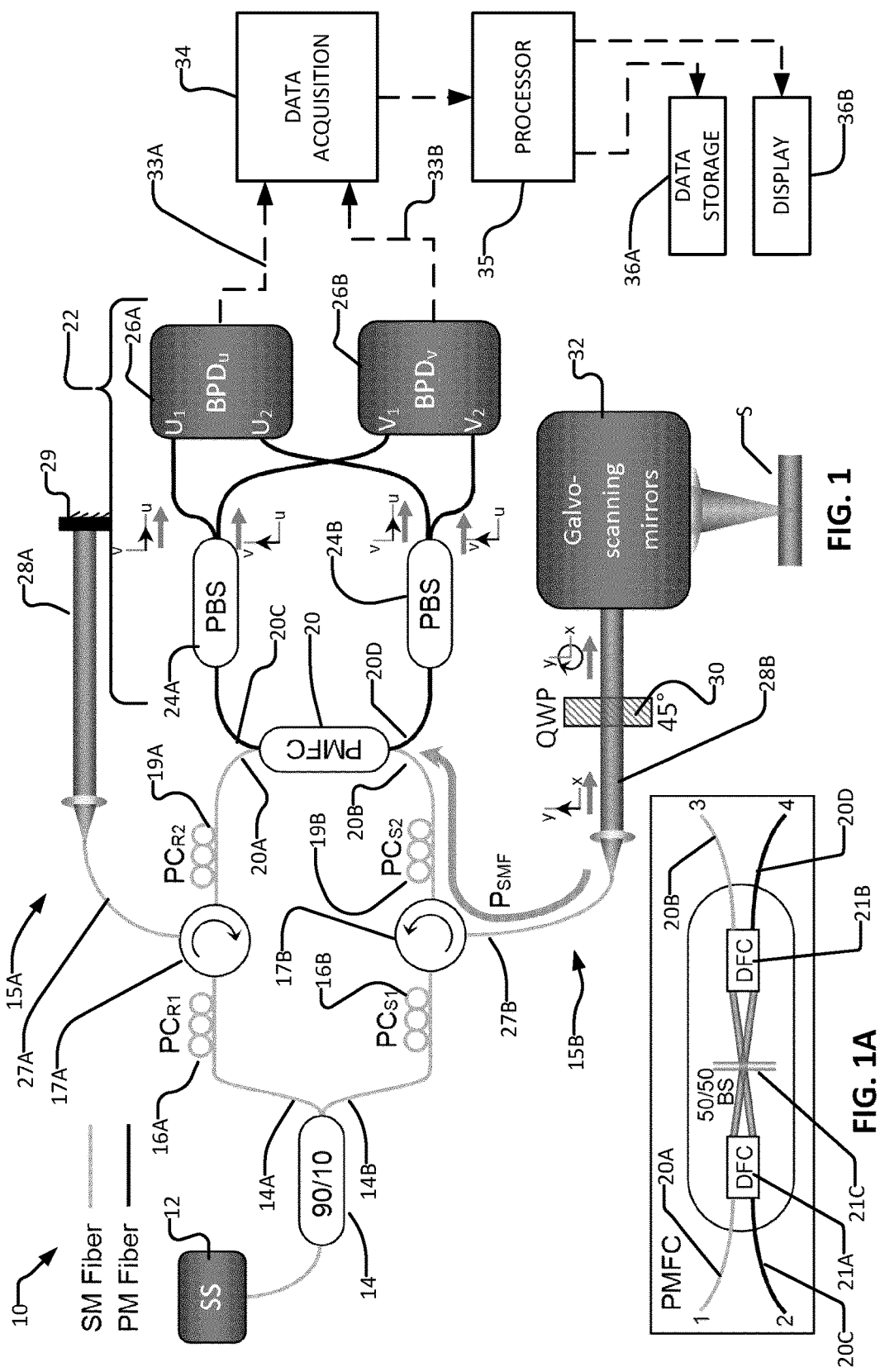
FIG. 1 is a schematic illustration of an example PS-OCT system.
FIG. 1A is a schematic illustration of an example optical combiner.

FIG. 1 is a schematic view of a fiber-based PS-OCT system 10 according to an example embodiment. System 10 is made up primarily of fiber-based passive components. System 10 does not require any active polarization modulating components.

System 10 comprises a suitable light source 12 that directs light into a Mach-Zehnder interferometer indicated generally by 13. Interferometer 13 includes a light splitter 14. Light from light source 12 is split between first and second outputs 14A and 14B of light splitter 14. Light from first output 14A of light splitter 14 is directed into a reference arm 15A by way of a polarization controller 16A and a circulator 17A. Light from a second output 14B of light splitter 14 is directed to a sample arm 15B by way of a polarization controller 16B and a circulator 17B.

Light returning from reference arm 15A and sample arm 15B is combined at an optical combiner 20 where optical interference occurs. In the illustrated embodiment, light returning from reference arm 15A is directed by circulator 17A to a first input 20A of combiner 20 by way of polarization controller 19A. Light returning from sample arm 15B is directed by circulator 17B to a second input 20B of combiner 20 by way of polarization controller 19B.

Light output by optical combiner 20 is detected by a light detector 22. In the illustrated embodiment, detector 22 comprises a polarization diversity detector. The illustrated detector comprises polarization beam splitters 24A and 24B (collectively beam splitters 24) respectively coupled to receive light from outputs 20C and 20D of optical combiner 20. Polarization beam splitters 24 each separate received light into two different polarization states which are preferably orthogonal polarizations. Light of a first one of the polarization states is directed from each of beamsplitters 24 to a first light detector 26A. Light of a second one of the polarization states is directed from each of beamsplitters 24 to a second light detector 26B.

In reference arm 15A, light is carried by an optical fiber 27A to a free-space section 28A. In free-space section 28A, light is coupled out of optical fiber 27A into a collimated beam which is reflected by a mirror 29 and coupled back into optical fiber 27A.

In sample arm 15B, light is carried by an optical fiber 27B to a free-space section 28B. In free-space section 28B, light is coupled out of optical fiber 27B, reflected by a sample S (e.g. a volume of tissue in vivo) and coupled back into optical fiber 27B. An optical component 30 (e.g. a quarter-wave plate) causes light incident on sample S to be circularly polarized. A scanner 32 changes the direction in which the light is projected onto sample S.

Light source 12 is a source of coherent light, for example a laser. In some embodiments light source 12 comprises a wavelength-swept laser. Sweeping the wavelength of the light source facilitates determination of reflection as a function of depth in sample S, as described for example below. A wide range of swept-wavelength lasers suitable for use in OCT are available. These include lasers which achieve wavelength sweeping by way of polygon scanner wavelength filters, Fabry-Perot tunable filters, dispersion tuning, and other approaches. Output of an optical detector over a full range of swept wavelength is typically called an "A-line".

Light source 12 emits light in the infrared part of the spectrum. For example, light source 12 may emit light having wavelengths of 750 nm or longer. In some embodiments light source 12 emits light in the wavelength range of 800 to 1500 nm or 800 nm to 2000 nm. In an example embodiment the emitted light has a wavelength in the range of 1270 nm to 1370 nm. In some embodiments the light is swept so that its wavelength varies over a suitable range of wavelengths (e.g. 50 to 200 nm). In an example embodiment the light has wavelengths that sweep over a wavelength range of 100 nm centered at 1320 nm. Light output by light source 12 may be narrowband laser light.

In system 10 it is notable that in is not necessary for any of the optical fibers upstream from (toward light source 12 from) coupler 20 to be polarization maintaining (PM) optical fibers. For example, the optical fibers upstream from coupler 20 may comprise non-polarization-maintaining optical fibers such as ordinary single-mode optical fibers. Furthermore, it is not necessary for the lengths of these upstream optical fibers to be matched with any degree of precision. Optical fibers downstream from coupler 20 (toward light detectors 26A and 26B) are PM optical fibers. It is optional and not mandatory for the optical fibers that carry light from polarizing beam splitters 24A and 24B to light detectors 26A and 26B to be PM optical fibers. The design of system 10 does not require any active polarization modulating components.

A PM optical fiber is constructed in such a way as to maintain the polarization of light being carried by the optical fiber. This is in contrast to an ordinary single mode optical fiber in which deviations from perfect symmetry within the fiber can cause significant crosstalk between different polarization modes. A typical PM optical fiber has a non-cylindrically-symmetrical construction with a cross-section that has two orthogonal symmetry axes such that only two distinct orthogonal polarization modes can propagate along these axes within the fiber. PM fibers are usually fabricated by providing stress members which induce birefringence which creates the two orthogonal propagation axes. These polarization modes experience very little crosstalk such that if linear polarized light is launched along one of the axes, it remains linearly polarized along that axis at the other end of the fiber. One embodiment of PM fiber is a so-called PANDA fiber. Some PM fibers have a normalized cross-talk of <30 dB after 100 m. PM1300-XP PANDA fiber is an example. A port for receiving a PM fiber typically has a configuration such that the fiber couples to the port with its propagation axes in a predetermined and repeatable orientation relative to the port.

Coupler 20 may be a 50/50 optical coupler in which first and second inputs 20A, 20B are configured to receive light from single-mode optical fibers and outputs 20C and 20D are configured to deliver light to PM optical fibers. In an example embodiment, an optical beam entering each of ports 20A and/or 20B of coupler 20 is collimated by one side of a corresponding dual fiber collimator (DFC) 21A, 21B. The resulting beams cross and are divided into two roughly equal output beams at a non-polarizing beamsplitter 21C. The output beams are subsequently coupled to output ports 20C and 20D by second sides of DFCs 21A and 21B.

The orientations of the PM optical fibers connected to ports 20C and 20D are held fixed, for example by providing connectors on the PM optical fibers with keys which engage keyways of ports 20C and 20D. Fixing the polarization axes of the PM optical fibers with respect to ports 20C and 20D facilitates providing defined polarization axes for the two detection channels as described herein.

Light splitter 14 does not necessarily split light evenly into outputs 14A and 14B. It is typically beneficial to cause more light to be delivered to output 14B (for eventual delivery to sample arm 15B) than is delivered to output 14A (for eventual delivery to reference arm 15A). For example, light splitter 14 may deliver light to outputs 14A and 14B in a ratio of 30/70 or less. In some embodiments light splitter 14 provides light at outputs 14A and 14B with a power ratio of 10/90.

Signals 33A and 33B from light detectors 26 are suitably conditioned and digitized by data acquisition system 34. The resulting streams of data are processed by a processor 35 (which may for example comprise a programmable data processor executing software and/or suitably configured hard-wired and/or configurable logic circuits) to yield derived data and/or images for display on a display 36A and/or storage in a data store 36B.

System 10 can measure the retardation presented by sample S from the amplitudes of arbitrarily-oriented x- and y-components of the light reflected from the sample. This may be done independently of their phase relation which may be used for optics axis determination.

Example Prototype System

In a prototype embodiment, light source 12 comprises a wavelength-swept laser. More specifically a 30-mW polygon-scanner-based wavelength-swept laser source, built based on the method described in [27], with 106.8-nm bandwidth centered at 1321.4 nm with 40 kHz repetition rate. In the prototype, light splitter 14 was a single mode 90/10 splitter arranged to direct 10% of the source power to reference arm 15A and 90% of the source power to sample arm 15B.

In the prototype, polarization controllers 16A and 16B were part number PLC-M02-NC-7, from General Photonics, Chino, Calif., USA and circulators 17A and 17B were part number CIR-3-13-L-1-0, from AFW Technologies, Hallam, Australia.

In the sample arm of the prototype, light is collimated in free space, passed through a quarter-wave plate (part number QWP RABQ-1600 from ThorLabs, Newton, N.J.) twice after reflecting from the sample, and coupled back to optical fiber 27B. A Galvo-scanning mirror (GVS002 from Thor-Labs, Newton, N.J.) provides a 2D raster scan of the OCT beam on the sample.

In the prototype, coupler 20 is a custom 50/50 coupler having input ports comprising SMF28e fibers and outputs into PM fibers. Polarizing beamsplitters 24 were fiber-based polarizing beamsplitters part number POBS-1310-L-3-7-2, from AFW Technologies, Hallam, Australia. Light detectors 26A and 26B were balanced photo-detectors part numbers PDB420A from ThorLabs, Newton, N.J.

The light collimated in free space from the fiber in the sample arm is set y-polarized using the polarization controller 16B (x and y are the axes of a lab coordinate system, these axes may be arbitrarily-oriented perpendicular axes). With its optics axis oriented at 45° to the x-axis, the quarter-wave plate QWP creates a circularly-polarized incident light on the sample, making polarization measurements insensitive to the sample rotation as described in [4]. Light reflected from the sample is in general elliptically polarized.

In the prototype, polarizing beam splitters 24 are PM-fiber based polarizing beam splitters. These beam splitters separate the two orthogonal polarizations aligned and perpendicular to the stress members of the PM fibers (assuming u-v axes to be coordinates relative to the PM fibers). Axes, u and v, of the PM fibers are not automatically aligned with the x-y lab coordinates. Polarization controller 19B can be set such that the x-polarized light power is directed to the u-detection channel (PBD$_u$—corresponding for example to light detector 26A) and y-polarized light is directed to the v-detection channel (PBD$_v$—corresponding for example to light detector 26B).

Polarization controllers 16A and 19A may be adjusted to balance the amplitude of the signal reflected from the mirror in reference arm 15A at the two detection channels PBD$_u$ and PBD$_v$ so that the two orthogonal polarizations of the reflected light from the mirror in the reference arm contribute equally in the two detection channels which, in turn, allows for measuring retardation of sample S. In the prototype, all optical fibers were fixed to an optical breadboard to ensure stable light polarization states throughout the system.

Example Calculations

The following description explains one way to process signals from light detectors 26 to obtain a measure of sample retardation. Such signal processing may be performed, for example by a programmable data processor of an imaging system. This example uses a Jones Matrix formalism. Assuming the sample being imaged is uniaxially anisotropic, the propagation of light in the sample can be modeled by its retardation and optics axis through the following Jones matrix:

$$M_S = R(-\Psi_S)WR(\Psi_S) = \begin{bmatrix} \cos(\Gamma_S/2) - \\ i\sin(\Gamma_S/2)\cos(2\Psi_S) & -i\sin(\Gamma_S/2)\sin(2\Psi_S) \\ -i\sin(\Gamma_S/2)\sin(2\Psi_S) & \cos(\Gamma_S/2) + \\ & i\sin(\Gamma_S/2)\cos(2\Psi_S) \end{bmatrix} \quad (1)$$

where $M_S$ is the Jones matrix, R is the coordinate rotation matrix, $\psi_S$ is the optics axis angle with respect to the x-y coordinate system (the lab coordinate system) and W is the retardation matrix expressed as $$W = \begin{bmatrix} e^{-i\frac{\Gamma_S}{2}} & 0 \\ 0 & e^{-i\frac{\Gamma_S}{2}} \end{bmatrix} \quad (2)$$

where $\Gamma_S$ is the sample retardation. The light coming out of the fiber in the sample arm is set y-polarized using polarizer 16A. Therefore, the polarization state of the reflected light being coupled back to the fiber in the sample arm at the tip of the fiber will be $$E_{BSc}^S = M_{QWP}M_S^2 M_{QWP}\begin{bmatrix} 0 \\ 1 \end{bmatrix} = \begin{bmatrix} -i\cos(\Gamma_S) \\ i\sin(\Gamma_S)e^{i2\Psi_S} \end{bmatrix} \quad (3)$$

where $M_{QWP}$ is the Jones matrix of quarter-wave plate 30 through which the light passes twice in the sample arm. The back-scattered light from the sample is coupled back to the fiber and is combined with the reflection from the reference arm by coupler 20. The polarization state of the light propagating in the path from the tip of the sample arm fiber 27B to input 20B of coupler 20 (path $P_{SMF}$ in FIG. 1) is not preserved due to the birefringence of the optical fibers through which the light is carried (SMF28 fibers in the prototype embodiment). Invoking time reversal symmetry and the principle of reciprocity, the Jones matrix of this path is unimodular provided the loss is negligible and can be expressed as:

$$M_{SMF} = \begin{bmatrix} a_S & b_S \\ -b_S^* & a_S^* \end{bmatrix} \quad (4)$$

where $a_S$ and $b_S$ are two complex unknown numbers modeling the birefringence of fiber path $P_{SMF}$. However, if polarization controller 19B is set to direct the x-polarized component of light reflected from the sample to the detection channel 26A and the y-polarized component to the detection channel 26B, the unknown number $b_S$ becomes zero, reducing the $M_{SMF}$ to $$M_{SMF} = \begin{bmatrix} a_S & 0 \\ 0 & a_S^* \end{bmatrix} \quad (5)$$

with only one unknown, namely, $a_S$. Therefore, the polarization of the reflected light from the sample at the detection channels is $$\begin{bmatrix} E_u^S \\ E_v^S \end{bmatrix} = M_{SMF} \begin{bmatrix} -i\cos(\Gamma_S) \\ i\sin(\Gamma_S)e^{i2\Psi_S} \end{bmatrix} = \begin{bmatrix} -i\cos(\Gamma_S)a_S \\ i\sin(\Gamma_S)e^{i2\Psi_S}a_S^* \end{bmatrix} \quad (6)$$

Balancing the contribution of the reflection from the reference arm to the two detection channels using the polarization controllers 16A and 19A permits measuring the sample retardation without knowing the unknown $a_S$. Assuming the amplitude of the reference arm reflection at the two detection channels is $|a_R|$, the ratio of the amplitudes of the two detection channels is $$\frac{|CH_v|}{|CH_u|} = \tan(\Gamma_S) \quad (7)$$

independent of $a_S$, $|a_R|$, and the sample optical axis angle $\Psi_S$. Therefore, the retardation can be measured by dividing the amplitudes of the two detection channels. The polarization independent structural information can be also be determined as $(CH_u^2 + CH_v^2)^{1/2}$.

Prototype System Tests

The performance of the prototype system was tested by imaging an achromatic quarter-wave plate, fingernail in vivo, and various samples of tissues ex vivo.

Figure 2A:
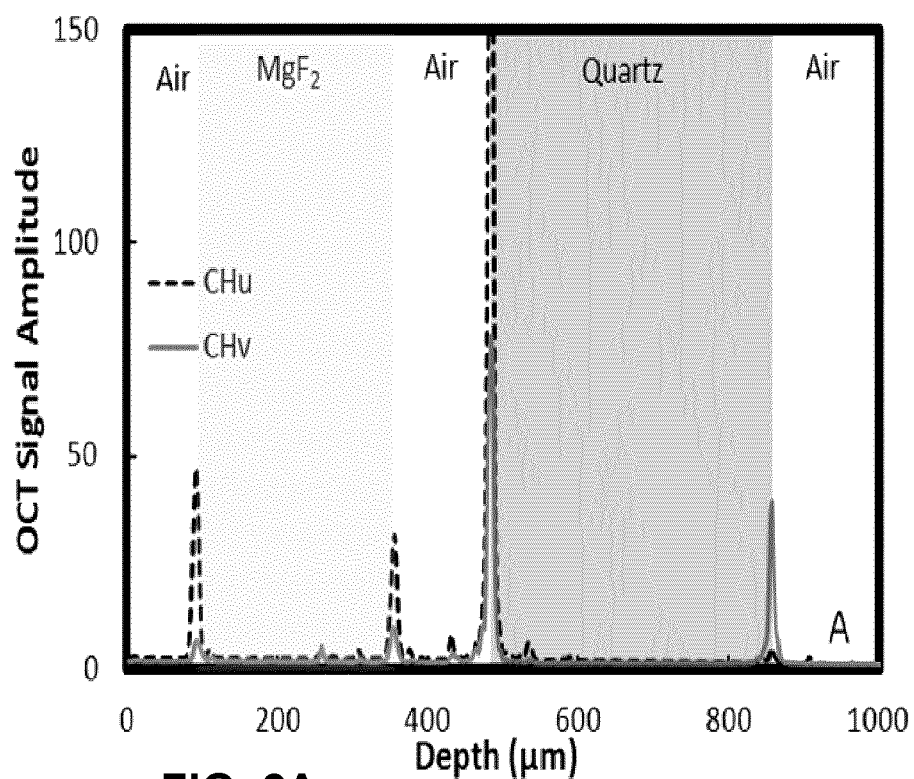
FIGS. 2A, 2B and 2C illustrate PSOCT imaging of a quarter-wave plate.

One test imaged a zero-order achromatic quarter-wave plate similar to the plate used for optical element 30 in sample arm 15B. The quarter-wave plate was constructed from two air-spaced multi-order waveplates, a crystal quartz plate and a magnesium fluoride plate, with their optical axes crossed. FIG. 2(a) shows the OCT signal amplitudes detected at the two detection channels ($CH_u$ in blue and $CH_v$ in red). There was a peak in the OCT signal amplitude corresponding to each surface interface. The expected polarization states of the reflection from the top and bottom surfaces of the quarter-wave plate can be obtained by inserting 0 and $\pi/2$ as $\Gamma_S$ in Eq. (6), respectively, resulting in an x-polarized reflection from the top surface and a y-polarized reflection from the bottom surface regardless of the optics axis orientation of the quarter-wave plate being imaged.

As shown in FIG. 2A, the u-detection channel has a large peak at the far left corresponding to the x-polarized top surface reflection and the v-detection channel has a large peak at the far right corresponding to the y-polarized bottom surface reflection, consistent with the expectations.

Figure 2B:
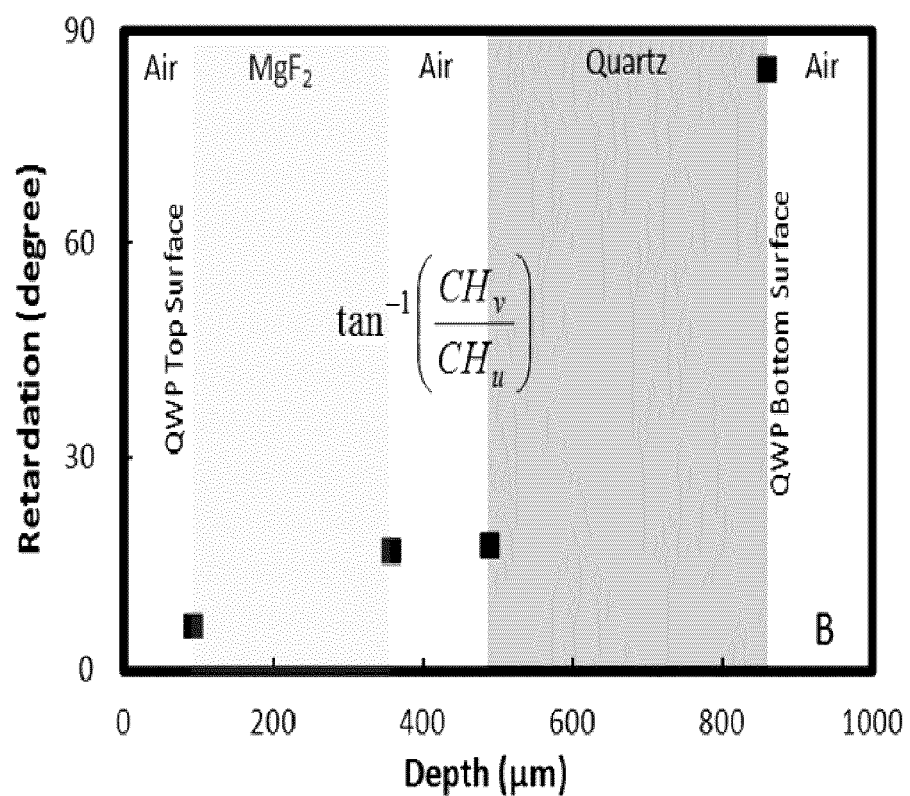
Figure 2C:
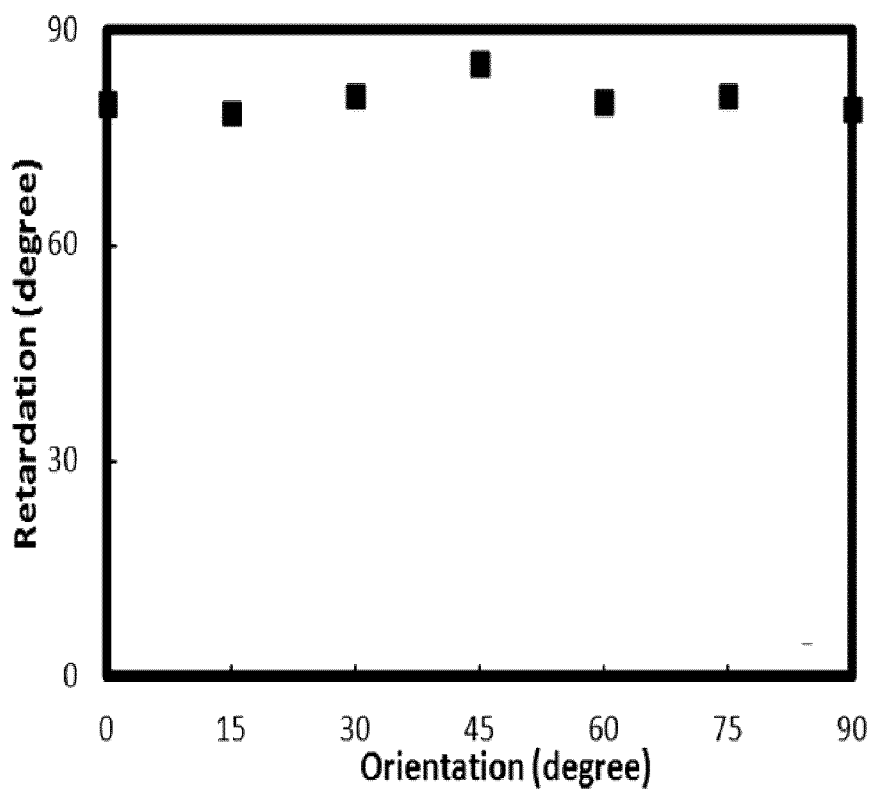

FIG. 2B shows the retardation of the quarter-wave plate measured from the OCT signal amplitudes of the u- and v-detection channels at the four surface interfaces. The retardation experienced by the reflection from the top surface was measured as being close to zero and the retardation experienced by the reflection from the bottom surface is measured as being close to 90°, consistent with the expectation values for a quarter-wave plate. The retardations experienced by the two surface interfaces in the middle of the quarter-wave plate are equal as expected since the quartz and MgF plates are air-spaced.

Figure 3:
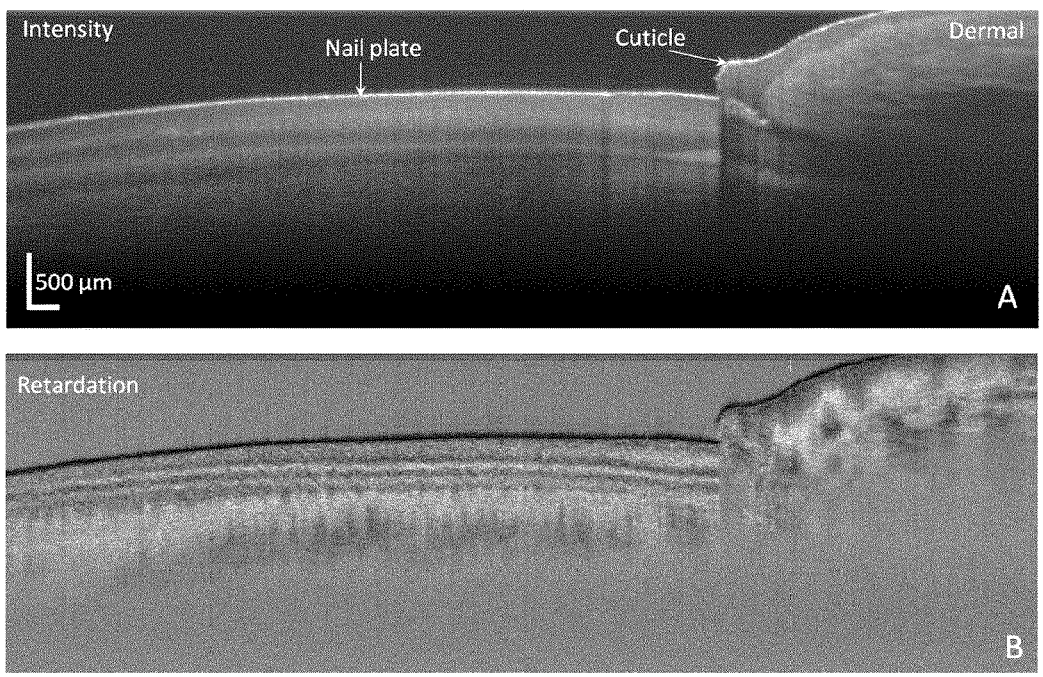
FIG. 3 illustrates intensity (a) and retardation (b) of fingernail obtained from PS-OCT imaging with a prototype system.

FIG. 3 shows the results of in vivo PS-OCT imaging of a fingernail with the prototype system. Different birefringence of the nail plate compared to the adjacent tissue is apparent, consistent with the results reported in [15, 25]. Birefringence of the fingernail was calculated to be 0.00615 from the average periodicity in the retardation image, resulting in 1.697°/μm retardation.

Rotary Probe OCT

The basic architecture illustrated in FIG. 1 may be used with alternative scanning and sample arm configurations. For example, that architecture may be applied to the case of rotary probe optical coherence tomography. System 10 is particularly advantageous for rotary OCT imaging because the detection system tends to mitigate the effects of rapidly changing polarization states as can occur when imaging with rotating fiber optic probes.

Figure 4:
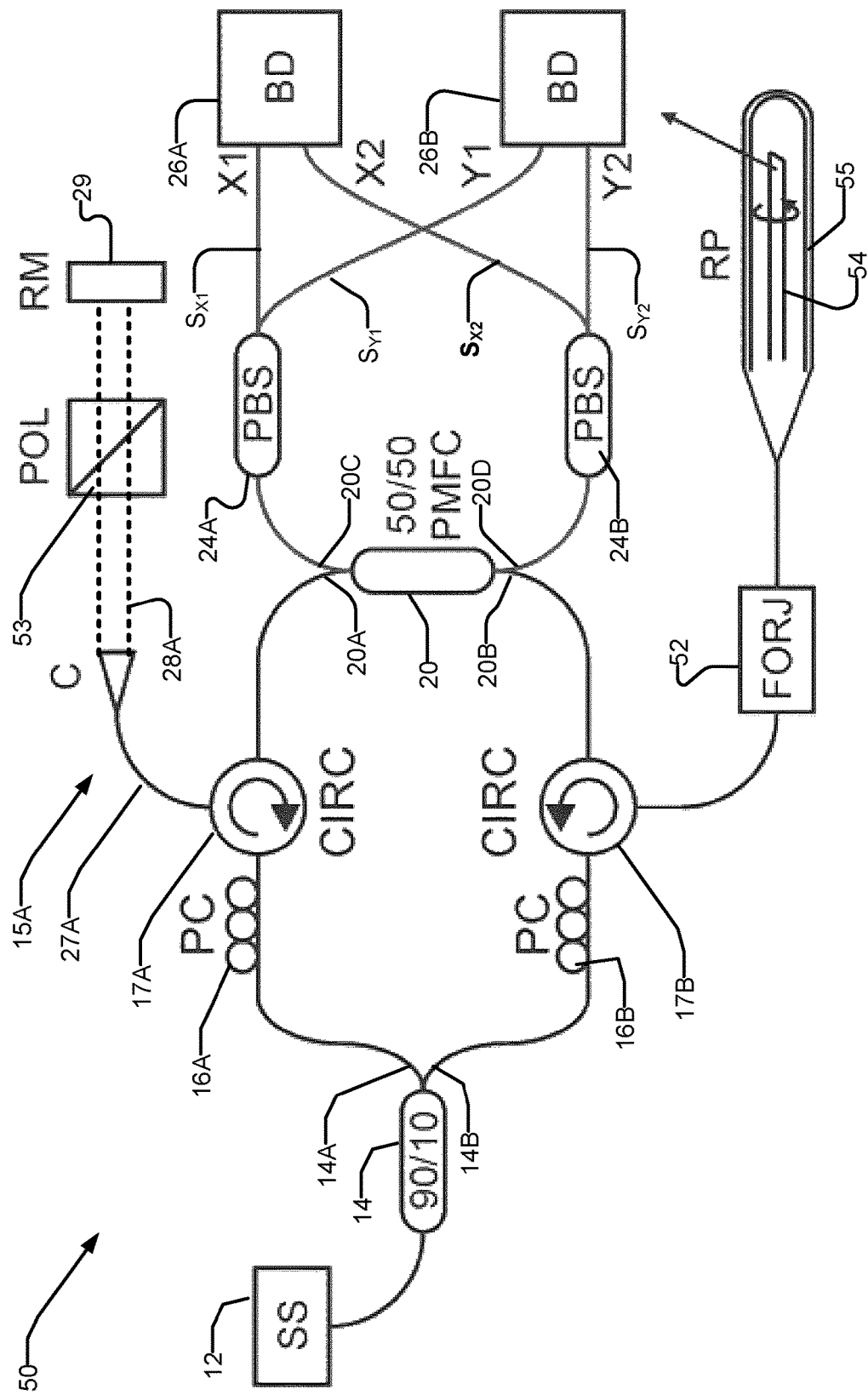
FIG. 4 is a schematic diagram illustrating an example endoscopic OCT system.

An example rotary probe OCT system 50 is shown schematically in FIG. 4. Components in FIG. 4 are labelled with the same reference numbers used to identify similar components in system 10 of FIG. 1. System 50 differs from system 10 primarily in that it includes a fiber optic rotary joint (FORJ) 52 and a specialized endoscopic probe 54 in sample arm 15B.

A prototype rotary probe OCT system used as light source 12 a 50.4 kHz swept source laser (SSOCT-1310, Axsun Technologies Inc., Billerica, Mass.) with 20 mW polarized output power centered at 1310 nm with 100 nm bandwidth (FWHM). Polarization controllers 16A and 16B were part number PLC-M02-NC-7 from General Photonics, Chino, Calif. These polarization controllers facilitate adjustment of the laser polarization prior to entry into sample and reference optical circulators.

Sample arm 15B of the prototype comprises a fiber optic rotary joint (part number MJP-SAPB from Princetel Inc of Pennington, N.J.) connected to a 0.9 mm diameter, rotationally-driven, side-looking fiber optic probe (C7 Dragonfly Imaging Catheter, St. Jude Medical Inc, St. Paul, Minn.). A custom built motor assembly was provided to facilitate rotational and pullback imaging capability.

A thin film polarizer 53 (LPNIR050, Thorlabs Inc., Newton, N.J.) mounted in a rotational mount is inserted before the end mirror of reference arm 15A. This polarizer is mounted at an angle to prevent reflection artifacts. The relative amount of light from the reference arm reaching each of detectors 26A and 26B is adjustable by setting polarizer 53 as described below.

Light beams returning from the sample and reference arms are combined at polarizing maintaining fiber coupler 20 which has single mode (SM) fiber inputs 20A and 20B, and polarization maintaining (PM) fiber outputs 20C and 20D. Outputs 20C and 20D are spliced to polarization beam splitters (PBS) 24. Polarization matched outputs from polarization beam splitters 24 are connected to 75 MHz balanced detectors 26A and 26B. In this prototype the detectors were part number PDB420C from Thorlabs Inc.

As is the case with system 10, the SM fiber inputs to coupler 20 obviate the need to match the optical path lengths of the X and Y OCT polarization channels upstream from coupler 20. Polarization maintaining fiber is used downstream from coupler 20 to ensure defined X and Y axes. A high speed digitizer (ATS9350, Alazar Technologies Inc., Pointe-Claire, QC) in 'k-clock' acquisition mode was provided to collect data. Custom written data acquisition software provided real time 2D OCT imaging.

In this prototype embodiment, balancing the reflected power of light from reference arm 15A into X and Y channels of the PDD setup is accomplished by minimizing the quantity $(S_{X1}+S_{X2}-S_{Y1}-S_{Y2})$. This may be done by adjusting the angle of reference arm polarizer 53. $S_i$ are the four slow monitor outputs on the balanced detector as shown in FIG. 4. This may be accomplished using a multichannel oscilloscope having on-board math functions. Due to spectral variation of the optical components, it may be difficult to completely balance the two detection channels over the entire laser sweep. An acceptable compromise, however, can be made by minimizing the integral of the above quantity over the entire laser sweep.

At this point, the PDD setup is balanced but the total power throughput of the reference arm may be reduced due to rejection by the polarizer. Power throughput of the reference arm may be increased by adjusting polarization controller 16A. Due to the spectral variation of the components along the reference arm through to the detectors, the PDD setup may become slightly unbalanced after power optimization. In this case, small adjustments to the setting of polarizer 53 may again restore X and Y balance.

Assuming $E_S$ and $E_R$ are the optical signals returning from the sample and reference arms, respectively, at the input ports 20A and 20B of combiner 20, the outputs of combiner 20 can be expressed as:

$$\vec{E}_1 = \frac{\sqrt{2}}{2}(\vec{E}_S + i\vec{E}_R) \quad (8)$$

$$\vec{E}_2 = \frac{\sqrt{2}}{2}(i\vec{E}_S + \vec{E}_R) \quad (9)$$

Polarization beam splitters 24 separate X and Y components of signals output by combiner 20, resulting in the following optical signals at the inputs of detectors 26A and 26B:

$$X_1 = \frac{\sqrt{2}}{2}(E_S \cos(\theta_S) + iE_{R,X}) \quad (10)$$

$$X_2 = \frac{\sqrt{2}}{2}(iE_S \cos(\theta_S) + E_{R,X})$$

$$Y_1 = \frac{\sqrt{2}}{2}(E_S \sin(\theta_S) + iE_{R,Y})$$

$$Y_2 = \frac{\sqrt{2}}{2}(iE_S \sin(\theta_S) + E_{R,Y})$$

where $\theta_S$ is the instantaneous angle of $E_S$ with the x-axis.

Therefore, with equal contributions to the two detection channels from the reference arm 15A, $(E_{R,X}=E_{R,Y}=E_R)$, the following expression is independent of $\theta_S$, providing images in which effects due to rotation-induced variations in polarization are suppressed:

$$I=\sqrt{I_X^2+I_Y^2} \quad (11)$$

If light entering reference arm 15A is relatively polarized, polarizer 53 may be replaced by a quarter-wave plate or half-wave plate. The use of a wave plate eliminates the need for polarization controller adjustment for reference arm power optimization.

Figure 5A:
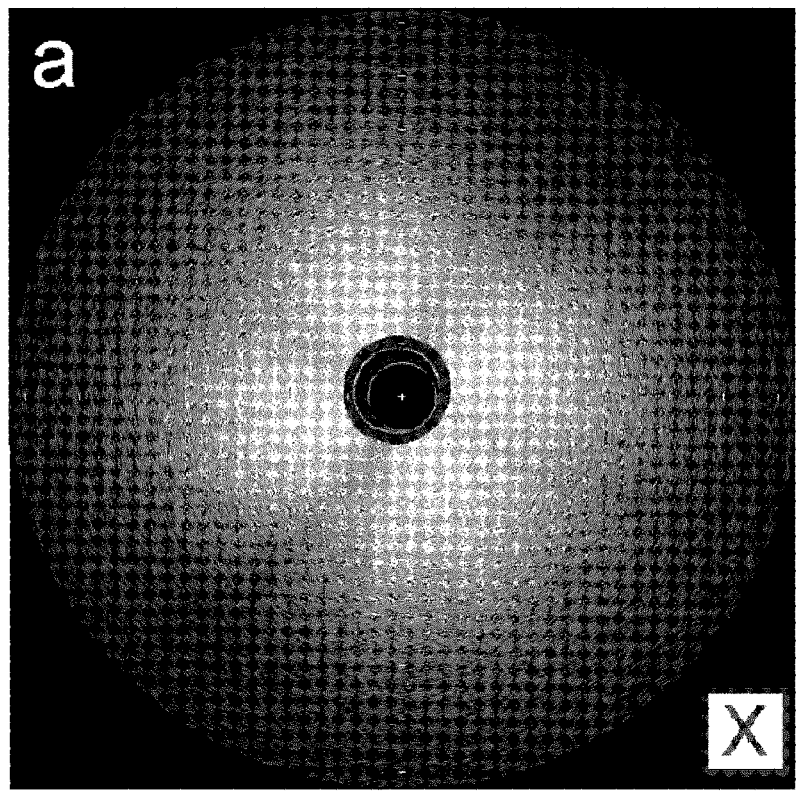
FIGS. 5A and 5B are polarization diverse images of a 1% Intralipid suspension.
Figure 5B:
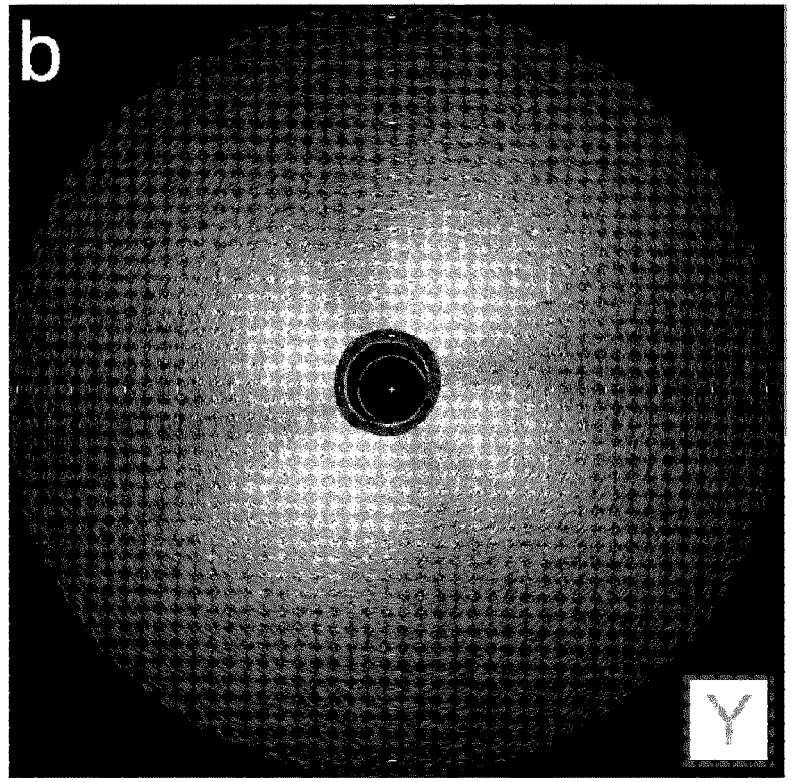
Figure 5C:
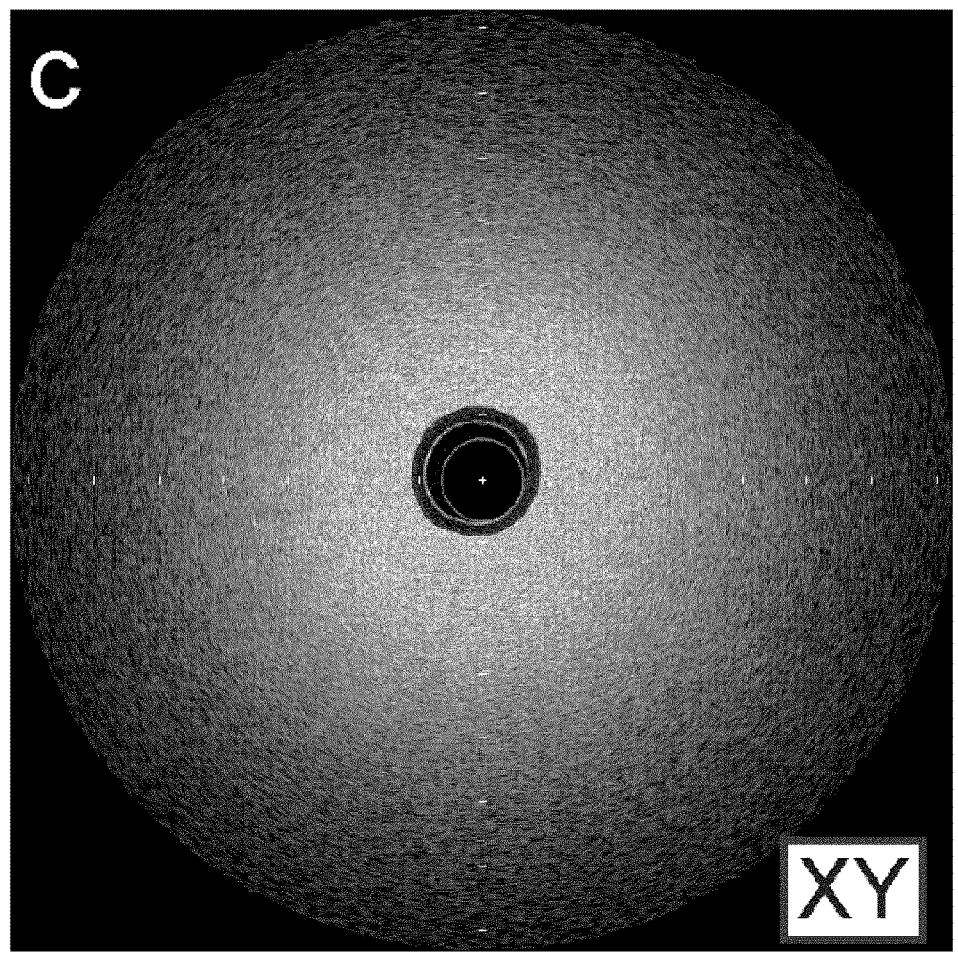
FIG. 5C is a polarization insensitive image of the suspension.

FIG. 5C is an example image taken by the prototype rotary probe OCT system of a 1% Intralipid suspension. As the suspension is isotropic, the image should have no variation with respect to the azimuthal coordinate. Images generated from the individual polarization channels X and Y, shown in FIGS. 5A and 5B respectively clearly show the varying polarization effect of the rotating probe creating variations in the intensity with respect to the azimuthal coordinate. In the polarization insensitive image shown in FIG. 5C, which was generated using Eq. 11, the variation of the intensity with respect to the azimuthal coordinate is clearly much reduced.

Figure 5D:
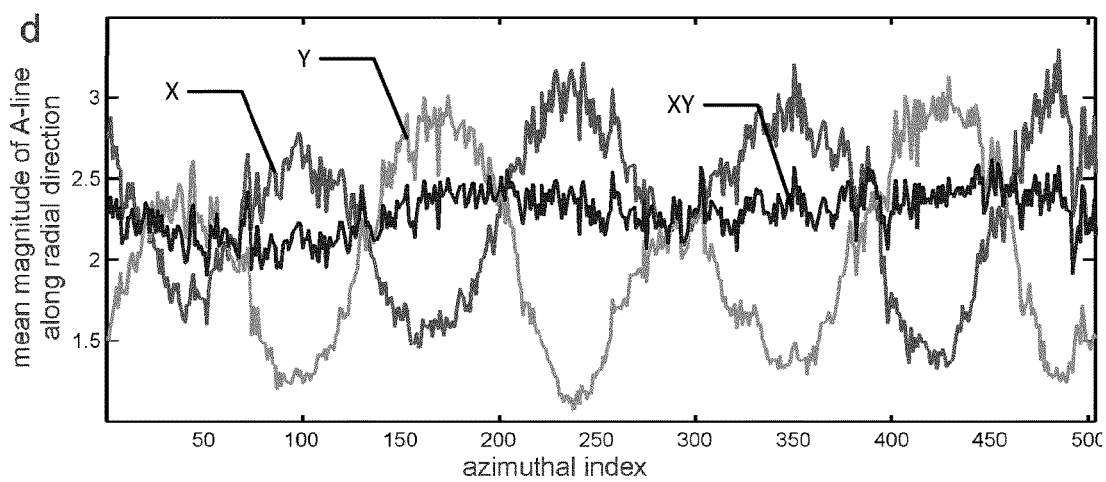
FIG. 5D is graph including plots of the average A-lines taken along the radial direction for the image shown in FIGS. 5A to 5C.

The intensity of the intralipid images averaged along the axial dimension, illustrated in FIG. 5D, clearly shows the suppressed polarization effects. For the image shown in FIG. 5C, the standard deviations of the axially integrated X and Y images (shown in FIGS. 5A and 5B) over the azimuthal coordinate are 0.48 and 0.54 respectively, much larger than that of the polarization insensitive image (0.14). Thus, the PDD detection reduces polarization variations in the image by a factor greater than 3.

Figure 6A:
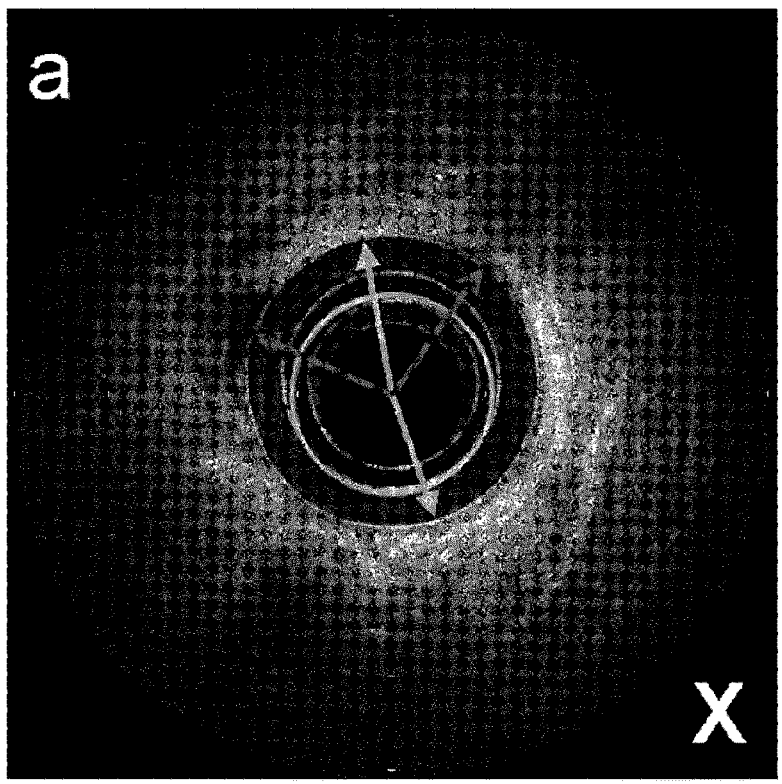
FIG. 6 shows OCT images of in vivo human airway. Images (a,b) are polarization diverse images. Image (c) is a polarization insensitive image of the human airway. Large positive and negative intensity variations in the X and Y images due to fluctuating polarization emitted from the rotating probe are indicated by arrows.
Figure 6B:
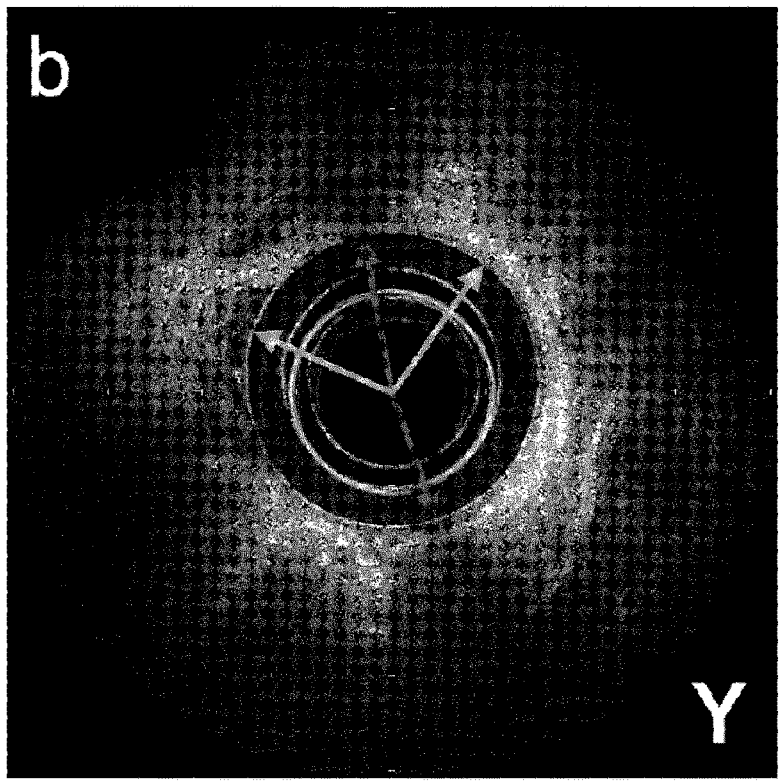
Figure 6C:
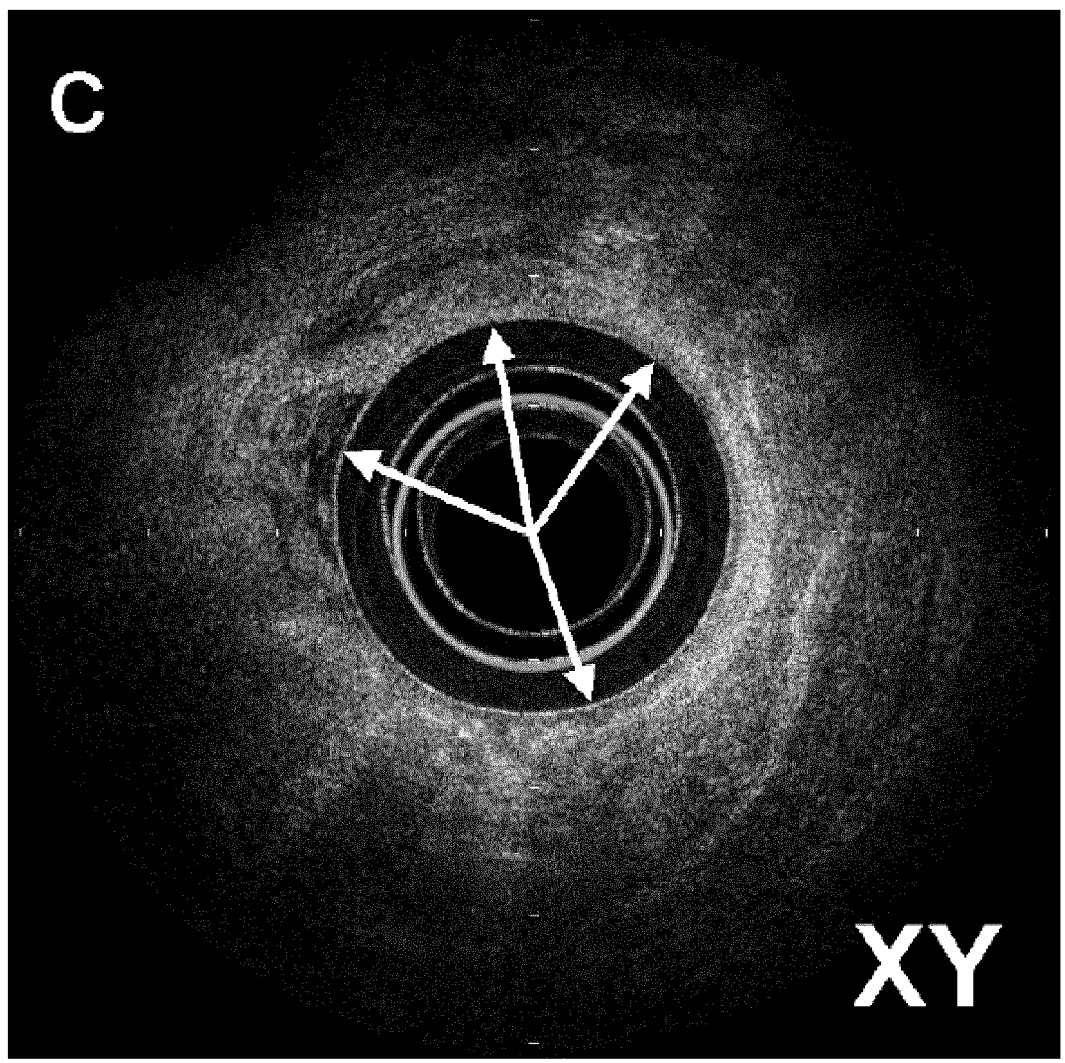

The prototype rotary probe OCT system was also used for in vivo lung imaging. In this situation, an additional closed ended sheath 55 was provided over the open-ended probe to prevent direct probe-patient contact. A bronchoscope was used to guide the OCT probe to an airway to be imaged. An image frame of in vivo human lung is shown in FIGS. 6A to 6C. FIGS. 6A and 6B respectively show X and Y polarization channel images. The polarization insensitive image is presented in FIG. 6C. The arrows in FIGS. 6A and 6B indicate regions where there is intensity trading between the two channels due to varying polarization emitted from the rotary probe. It is clear that PDD improves the ability to discern tissue morphology.

Co-Registered AF-OCT Systems

Systems as described herein may be modified to provide high-efficiency, fiber-based co-registered fluorescence-optical coherence tomography imaging systems. Such a system may be capable of imaging airways in vivo.

Implementing a combined fluorescence and OCT imaging system includes three main challenges: combining fluorescence excitation light (typically in blue or UV parts of the spectrum) and forward OCT light, splitting collected fluorescent emissions (which may, for example, comprise green light) from OCT back-scattered light, and providing a fiber optic rotary joint (FORJ) capable of supporting the distinct wavelength ranges used for fluorescence and OCT imaging. These challenges can be particularly acute in the case of AF-OCT imaging because collected autofluorescence emissions tend to be very faint.

Figure 7A:
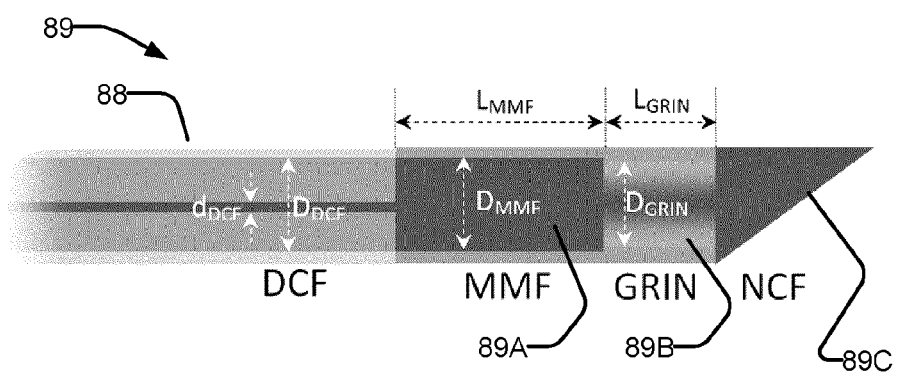
FIG. 7A is a schematic view of an example probe tip having enhancements for AF-OCT imaging.
Figure 7:
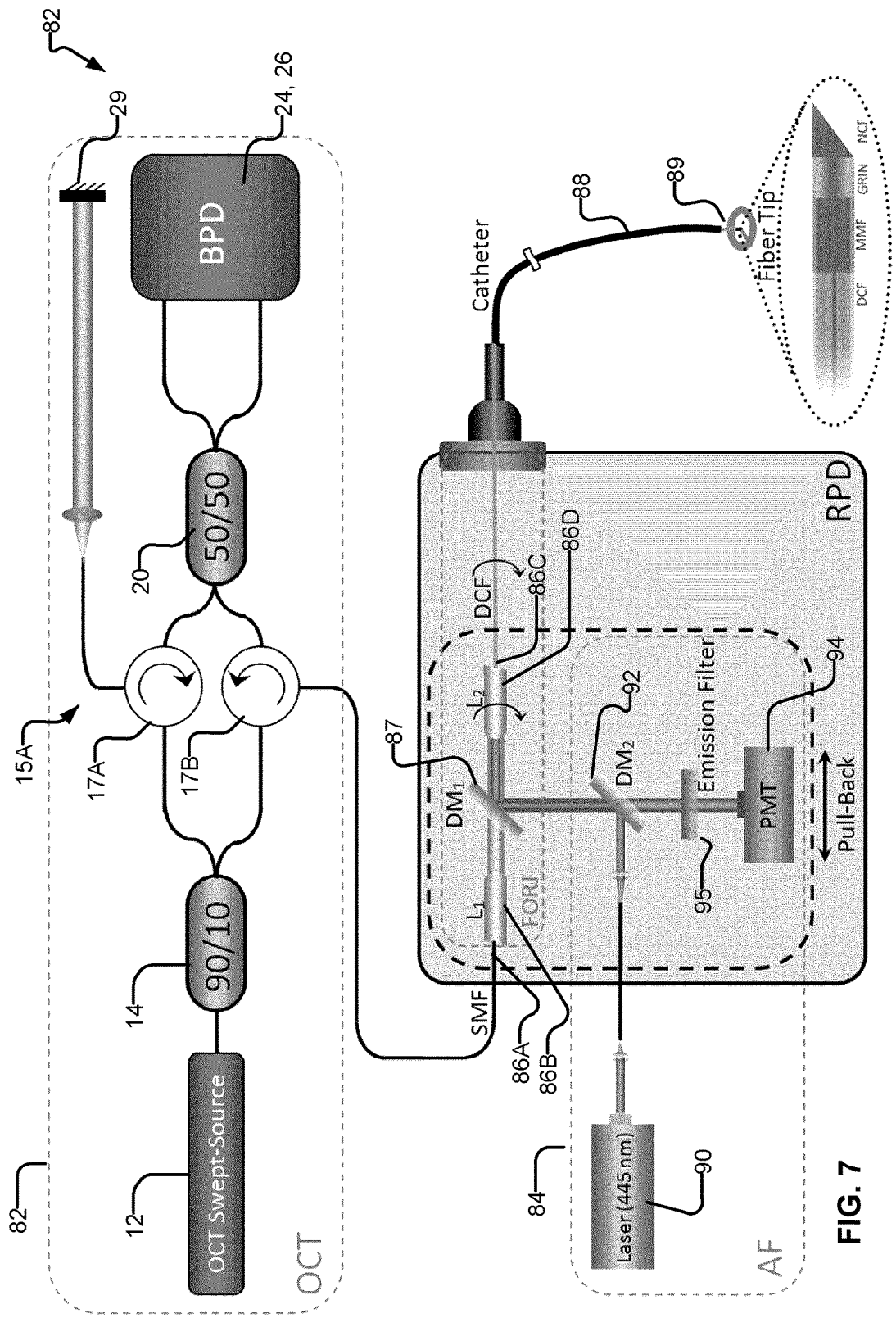
FIG. 7 is a schematic view of an example AF-OCT imaging system.

FIG. 7 is a schematic diagram showing an example double-clad fiber (DCF)-based dual-modality imaging system 80. System 80 includes an OCT subsystem 82 and a fluorescence imaging subsystem 84. OCT subsystem 82 may optionally provide polarization sensitive imaging but this is not mandatory. OCT subsystem 82 may be constructed like system 10 or 50 described above, for example. In some embodiments, OCT subsystem comprises an OCT subsystem of another suitable configuration. A wide variety of constructions for OCT systems are known to those of skill in the art.

System 80 comprises a FORT 86 which includes an embedded dichroic mirror 87. Mirror 87 separates light used for AF and OCT imaging. FORT 86 comprises a single mode fiber (SMF) port 86A connected to a stationary rod lens 86B, a dual clad fiber (DCF) port 86C connected to a rotary rod lens 86D and an embedded long-pass dichroic mirror 87. Mirror 87 transmits infrared (IR) light and reflects visible or UV light. Long-pass dichroic mirror 87 combines and separates the OCT and fluorescence light beams.

OCT light passes bidirectionally between SMF port 86A and DCF port 86C. Lens 86B collimates the forward OCT light to free space and couples back-scattered OCT light to the SMF port 86A. Infrared anti-reflection coating on lens 86B minimizes insertion loss. Lens 86D couples forward OCT light into the core of a DCF 88 and collimates the back-scattered OCT light in free space.

DCF 88 carries the OCT light to a probe tip 89. Probe tip 89 directs the forward OCT light onto a sample and captures OCT light that has been reflected from the sample. The captured OCT light is directed by probe tip 89 into the core of DCF 88 which carries the back-scattered OCT light to FORJ 86. The back-scattered OCT light passes through FORJ 86

Lens 86D also couples fluorescence excitation light (which is typically blue or UV light) into an inner cladding and/or core of DCF 88 and collimates fluorescence emission photons (which may be the result of autofluorescence) collected through the inner cladding of DCF 88 to free space. Lens 86D may be free of anti-reflection coating so that it can pass both visible and IR wavelength ranges.

Fluorescence imaging subsystem 84 comprises a light source 90 which emits fluorescence excitation light. The excitation light is directed into FORJ 86 by a dichroic mirror 92. Mirror 92 reflects excitation light but passes collected fluorescence light. Mirror 92 directs the excitation light onto mirror 87 of FORJ 86. Mirror 87 deflects the excitation light onto lens 86D which couples the excitation light into the inner cladding and/or core of DCF 88.

The core of DCF 88 carries the excitation light to probe tip 89. Probe tip 89 directs the excitation light onto the sample where it excites fluorescent emissions. The fluorescent emissions are typically at a longer wavelength than the excitation light. For example, for blue excitation light fluorescent emissions from autofluorescence typically comprise mainly green light. Some of the fluorescent emissions are captured by probe tip 89 as collected fluorescence light and coupled into DCF 88. The collected fluorescence light travels along the same path as the excitation light except in the reverse direction until the collected fluorescence light encounters dichroic mirror 92 which separates the collected fluorescence light from the excitation light. In the illustrated embodiment collected fluorescence light passes through mirror 92 to be detected by a light detector 94 such as a photo-multiplier (PMT)-based detector. In the illustrated embodiment an emission filter 95 is provided to block light other than collected fluorescence from reaching detector 94.

System 80 includes a mechanism for pulling back or rotating and pulling back DCF 88 in order to obtain 2D or 3D OCT images. To facilitate this, DCF 88 may be mounted in a torque cable that transfers rotational motion from a rotary pull back drive unit (RPDU) to the distal end.

Probe tip 89 may, for example, have the construction shown in FIG. 7A. This construction has advantages over existing probe tip designs for AF-OCT imaging. Probe tip 89 and DCF 88 form a probe assembly having a length suitable to reach a desired imaging location. For example, the probe may have a length of 0.7 to 2 meters in some embodiments. The distal end of DCF 88 is spliced to probe tip 89. Probe tip 89 comprises a step-index multimode fiber (MMF) 89A, a graded-index fiber (GRIN) 89B, and a light deflector such as an angle-polished no-core fiber (NCF) 89C. GRIN 89B focuses the AF excitation and OCT beams onto the sample.

MMF 89A has a large core diameter. Therefore, MMF 89A allows the forward OCT beam to expand so as to provide high numerical aperture at the specimen and, in turn, high lateral resolution for OCT imaging with a relatively long working distance. The length of MMF 89A is designed such that the forward OCT beam does not reach the cladding of MMF 89A as the OCT beam spreads out as it propagates along MMF 89A. The light deflector (in this example angle-polished NCF 89C) deflects the beams toward the side of probe tip 89.

MMF 89A plays different roles for OCT light and AF light. For OCT light the MMF allows expansion of the forward-going OCT beam to increase the numerical aperture of the following lens and, in turn, to provide high lateral resolution for OCT light with long working distance. For AF imaging, MMF 89A confines both the AF excitation light that is originally travelling within the DCF inner cladding and the collected AF light, enhancing the AF imaging power throughput.

In some embodiments the length of MMF 89A, $L_{MMF}$, is designed such that OCT light does not expand to reach the core diameter ($D_{GRIN}$) of GRIN 89B, or $$L_{MMF} \times \frac{2\lambda_{OCT}}{\pi w_{OCT} n_{OCT}} < D_{GRIN},$$

where $w_{OCT}$, and $n_{OCT}$ are respectively half of the mode field diameter of the core of DCF 88 and the refractive index of the core of MMF 89A at the OCT wavelength ($\lambda_{OCT}$). The core diameter of MMF 89A may be selected such that OCT light does not expand to reach the MMF cladding, or $$D_{MMF} > L_{MMF} \times \frac{2\lambda_{OCT}}{\pi w_{OCT} n_{OCT}}.$$

To maximize AF light throughput the MMF and GRIN core diameters are designed to be near to the DCF inner cladding diameter, or $$D_{MMF} \approx D_{DCF} \approx D_{GRIN}.$$

For example, an AF/OCT catheter made from DCF with $d_{DCF} \approx 9$ μm and $D_{DCF} = 105$ μm and 1310 nm OCT center wavelength, an MMF segment with 105 μm core diameter and 450 μm length could be a suitable choice. It is beneficial for the refractive index of the core of MMF 89A to match (or be very close to) the refractive index of the cores of DCF 88 and GRIN 89B.

In some embodiments, the light deflector deflects the beams through an angle θ that is less than 90 degrees with respect to the axis of probe 89 such that the deflected beam is somewhat forward-looking. This construction is advantageous for Doppler OCT imaging in small passages (such as bronchi) because blood vessels tend to extend along such small passages such that the flow velocity of blood in such vessels also tends to be more parallel to the small passages than perpendicular to the small passages. Doppler OCT images of better quality can be obtained when the direction of the OCT beam is more nearly parallel to the direction of blood flow as opposed to more nearly perpendicular to the direction of blood flow.

In AF imaging, MMF 89A confines the AF excitation light beam and the collected AF light so they do not escape from probe tip 89. Thus the provision of MMF 89 enhances the power efficiency of both delivery of AF excitation light and collection of AF emissions.

OCT and AF images may be constructed by processing the acquired data. OCT images may be constructed from the digitized A-line data stream acquired during a full or desired part of a rotational sweep. AF images may be constructed by averaging the digitized signal corresponding to the collected AF light over each A-line scan. Unlike OCT images, AF images do not provide resolved depth information. AF emissions from various depths contribute to the measured AF signal at each point. AF-OCT images may be illustrated either or both in polar coordinates (e.g. with the horizontal axis representing the azimuthal angle value (θ) and the vertical axis representing the depth information (r)) and Cartesian coordinates (e.g. coordinates equivalent to the x-y lab coordinate frame).

In alternative embodiments, other mechanisms are provided for deflecting light at probe tip 89 so that the light enters the sample. For example, in place of or in addition to angle-polished NCF 89C may be provided one or more of:
- a mirror of some other construction. The mirror may be fixed or driven to pivot or rotate;
- an offset-axis lens;
- a prism;
- a D-Fiber (i.e. a fiber having a "D" shaped cross-section so the deflected beam does become abberated with astigmatism;
- a ball lens combined with a mirror facet ground and polished on one side; and
- other deflection mechanisms that are known to those of skill in the art.

In alternative embodiments, other mechanisms are provided for focusing light at probe tip 89 instead of or in addition to GRIN 89B. For example, a focusing mechanism may comprise one or more of:
- a ball lens;
- a multi-element spherical lens system;
- an aspheric lens;
- a focusing mirror; and
- other focusing mechanisms that are known to those of skill in the art.

In some alternative embodiments the locations of OCT subsystem 82 and fluorescence subsystem 84 are switched. In such alternative embodiments mirror 87 is configured to reflect OCT light and to pass fluorescence excitation light and collected fluorescence light.

OCT-AF Prototype Embodiment

In a prototype embodiment constructed as shown in FIG. 7, OCT light source 12 was a 50.4 kHz wavelength-swept laser source (SSOCT-1310, Axsun Technologies Inc., Billerica, Mass.) with 20 mW output power centered at 1310 nm with 100 nm bandwidth (FWHM). OCT light detectors 26A and 26B were provided by a balanced photodetector (PDB420A, ThorLabs, Newton, N.J.). Output signals from light detectors 26A and 26B were fed into one channel of a digitizer card (ATS460, AlazarTech, Pointe-Claire, QC) to provide a data stream for signal processing and creating OCT images.

In the prototype embodiment AF light source 90 was a 445 nm semiconductor laser providing about 7 mW optical power on the sample after the fiber probe (CUBE 445-40C, Coherent, Santa Clara, Calif.). Light detector 94 was a PMT-based detector (H9433-201, Hamamatsu, Japan). An output signal from the PMT-based detector was fed into a second channel of the digitizer card to acquire data stream corresponding to the AF signal.

In the prototype, AF and OCT datasets are acquired simultaneously in polar coordinates (where r and θ are the depth and azimuthal coordinates) while the probe is being rotated and pulled back. Acquisition and processing of the datasets is performed by a processor executing custom data acquisition software. The software generates an immediate OCT display with corresponding AF and Doppler signals overlaid. Doppler images were created from the OCT data stream using an intra-line color Doppler algorithm as described in [83]. As no depth information is encoded in the AF dataset, each AF data point is averaged over the length of the OCT A-line. The custom data acquisition software also generates a real time z-θ map of AF signal during the pullback (z coordinate is the pullback dimension).

Mirror 87 was a dichroic beamsplitter. Mirror 92 was an emission filter (E480LPXT, Chroma, Bellows Falls, Vt., USA). Custom software processed the data to provide real-time 2D AF-OCT imaging.

The total insertion loss of a prototype AF-OCT FORJ was measured to be 0.5 dB, 2 dB, and 0.8 dB at OCT (1310 nm), blue (445 nm), and green (550 nm) wavelengths, respectively. Since AF emissions are mostly in the green wavelength range for normal tissue, the insertion loss is measured at 550 nm to evaluate the FORJ performance for AF emissions. Since the AF emission power is usually small, it is very important to separate AF emissions from back-scattered OCT light without significant loss. The measured insertion loss values confirm that the prototype AF-OCT system has high AF power efficiency.

The prototype had a DCF probe including a 1.5 m-long DCF (FUD-3489, Nufern, East Granby, Conn.). The probe had a diameter of 508 µm, allowing imaging in small airways. The spot size of the probe was measured to be $[2w_{0x}, 2w_{0y}]$=[16 µm, 24 µm] and [53 µm, 60 µm] at 1310 nm and 445 nm, respectively, with 750 µm±50 µm working distance measured from the end of GRIN 89B. A stationary plastic sheath with 0.9 mm outside diameter covers the DCF probe to prevent the probe from contacting the structures being imaged.

Example AF-OCT Images

Figure 8:
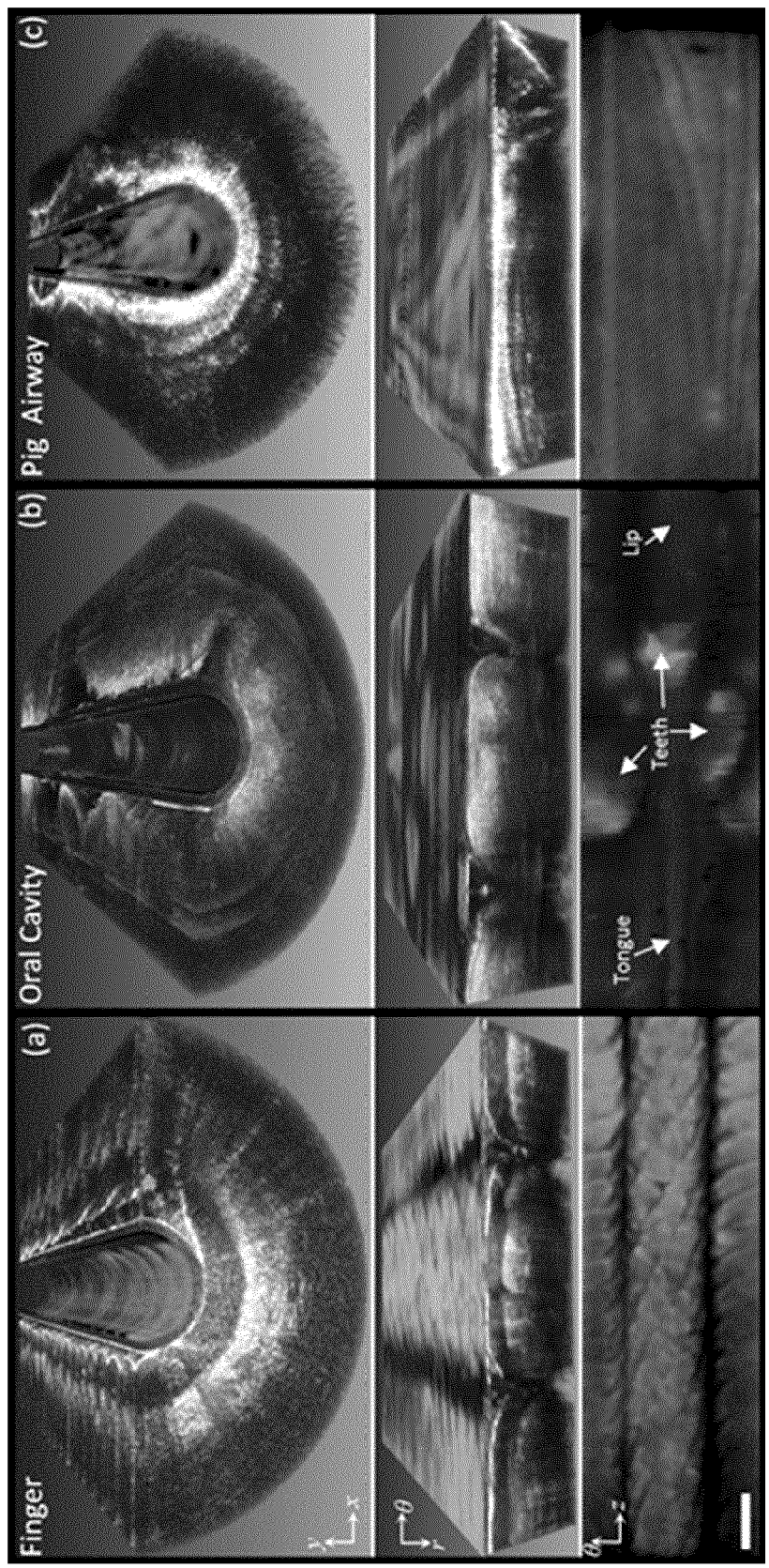
FIG. 8 is a group of volumetric AF-OCT images in Cartesian (top row) and polar (middle row) coordinates with corresponding unwrapped AF images (bottom row). The images are of fingers (first column), inside an oral cavity (second column), and a pig airway ex vivo (third column). The white bar is 1 mm
Figure 9:
FIG. 9 is an unwrapped AF image of a human airway obtained by AF-OCT imaging in vivo. Inset images are AF-OCT images corresponding to lines indicated in the main image.

FIG. 9 presents the results of imaging finger pads, inside oral cavity, and in pig airways ex vivo; the top and middle rows show volumetric OCT images with AF images overlaid in Cartesian (cut in half) and polar (full image) coordinates. The bottom row shows AF images constructed from AF signals in the rotational sweep along the whole pullback length. For the images shown in FIG. 8 the probe was rotated at 5 rpm in 10 mm pullback length with 0.2 mm/s pullback speed inside the stationary plastic sheath.

To image the finger pads, AF-OCT imaging was carried out while a subject grasped the plastic sheath at the distal end of the probe with two fingers. To image the oral cavity, the DCF probe inside the plastic sheath was placed inside a volunteer's oral cavity. The end of the probe was located at the tip of the tongue so that tongue, teeth, and lips were covered in 10 mm pullback. The oral cavity was closed during the imaging. The pig airways were imaged in a whole fresh lung harvested from a pig. The DCF probe with the plastic sheath was inserted into the pig lung through the trachea and pushed forward until it reached the pig airways where AF-OCT imaging was carried out.

The AF-OCT imaging system was also used for in vivo human lung imaging. A bronchoscope guided the OCT probe to the imaged airway. FIG. 9 shows an AF image constructed from AF signals acquired in the rotational sweeps along the pullback length. The insets in FIG. 9 show AF-OCT images corresponding to the dashed lines in the AF image. The far left of the AF image corresponds to airway tissue with alveoli located at the distal part of the lung and the far right of the AF image corresponds to more proximal airway tissue. In the AF image, the airway tissue with alveoli is clearly different from the more proximal bronchus tissue. A strong AF signal at the far right of the AF image created by the cartilage band located near the luminal surface indicates that cartilage bands are highly fluorescent. This is consistent with the results on ex vivo human airway sections presented in [41].

The relative AF emission from the lung components represents the fluorophore contents of the components that, in turn, are related to the density of collagen and elastin fibers present in the tissue. The biochemical information about the tissue co-localized with the structural information obtained from AF-OCT imaging can be used for pathogenesis applications. For instance, this method may be applied to observe changes in AF signals of different lung tissue components. Such changes may be caused by early cancer development. By providing biochemical information about tissue co-localized with structural information, an AF-OCT system as described herein can provide several diagnostic applications, for instance, to study changes in biochemical and structural properties of tissue associated with disease processes in lung and other organs.

The increased spatial resolution and sensitivity of the prototype apparatus facilitated by the provision of a probe including a clad spacer (e.g. MMF 89A of FIG. 7A) allowed the prototype apparatus to obtain AF images showing vasculature within very small airways in vivo. In one set of experiments a number of patients underwent flexible bronchoscopy under local anesthesia applied to the upper airways and conscious sedation. Radial endobronchial ultrasound (R-EBUS) was used to localize peripheral nodules. The R-EBUS probe was an Olympus EU-MEL UM-S20-17S 20 MHz Endoscopic Ultrasonic Probe, Olympus America Inc. The R-EBUS probe was deployed inside a guide sheath through the working channel of a bronchoscope into the airways of interest with or without the guidance of the virtual bronchoscopy navigation system (Bronchus LungPoint Virtual Navigation System, Broncus Medical, Inc. Mountain View, Calif., USA). The R-EBUS probe was then withdrawn while the guide sheath was left in place to register nodule location for AF/OCT imaging. Saline flushing and suctioning were applied to the airways before AF/OCT imaging to reduce the effects of bronchial secretions and small bleeding on optical imaging. AF/OCT scans were carried out on the lesions by the AF/OCT catheter of the prototype device inserted through the R-EBUS guide sheath.

Depending on the required information, different scanning parameters including the rotational and pullback speeds and the pullback length were set by the custom software. For instance, Doppler OCT scans can require high-density A-scans/frame and, in turn, low rotational speed. All Doppler OCT (DOCT) scans were performed with 12.5 cycle per second rotational speed and 4032 A-scans per frame. In the majority of the cases, AF/OCT scans were also carried out outside lesions on presumably-normal airways (based on CT-scans) to provide normal control samples. In some cases multiple scans were performed on the same locations to ensure the reproducibility of imaging. At the final stage of the procedure biopsies, brushing, and washing were performed on lesions through the guide sheath after removing the AF/OCT catheter. The AF/OCT scans added 5 to 10 minutes to the standard procedure time and all patients tolerated the procedure well with no complications such as hemorrhage or pneumothorax.

Abnormal tissue areas showed significantly reduced AF signals as compared to normal areas. Dark areas in the AF map along a pullback were considered to be high-risk areas. Epithelial thickening, alveolar wall thickening/alveolar collapse, basement membrane disruptions, and the lack of normal lung parenchymal structures were observed in OCT images that were identified as being abnormal.

FIG. 10 shows imaging results from in vivo endoscopic AF/OCT scans from three airway sections with high-density vasculature. To include Doppler contrast the two pullbacks corresponding to the results illustrated in FIG. 3a and FIG. 3b were carried out at lower rotational speed (12.5 Hz) with high-density A-scans per frame (4032 A-scans/frame) compared to the pullback whose results are presented in FIG. 3c (25 Hz rotational speed; 1008 A-scans/frame).

Figure 10A:
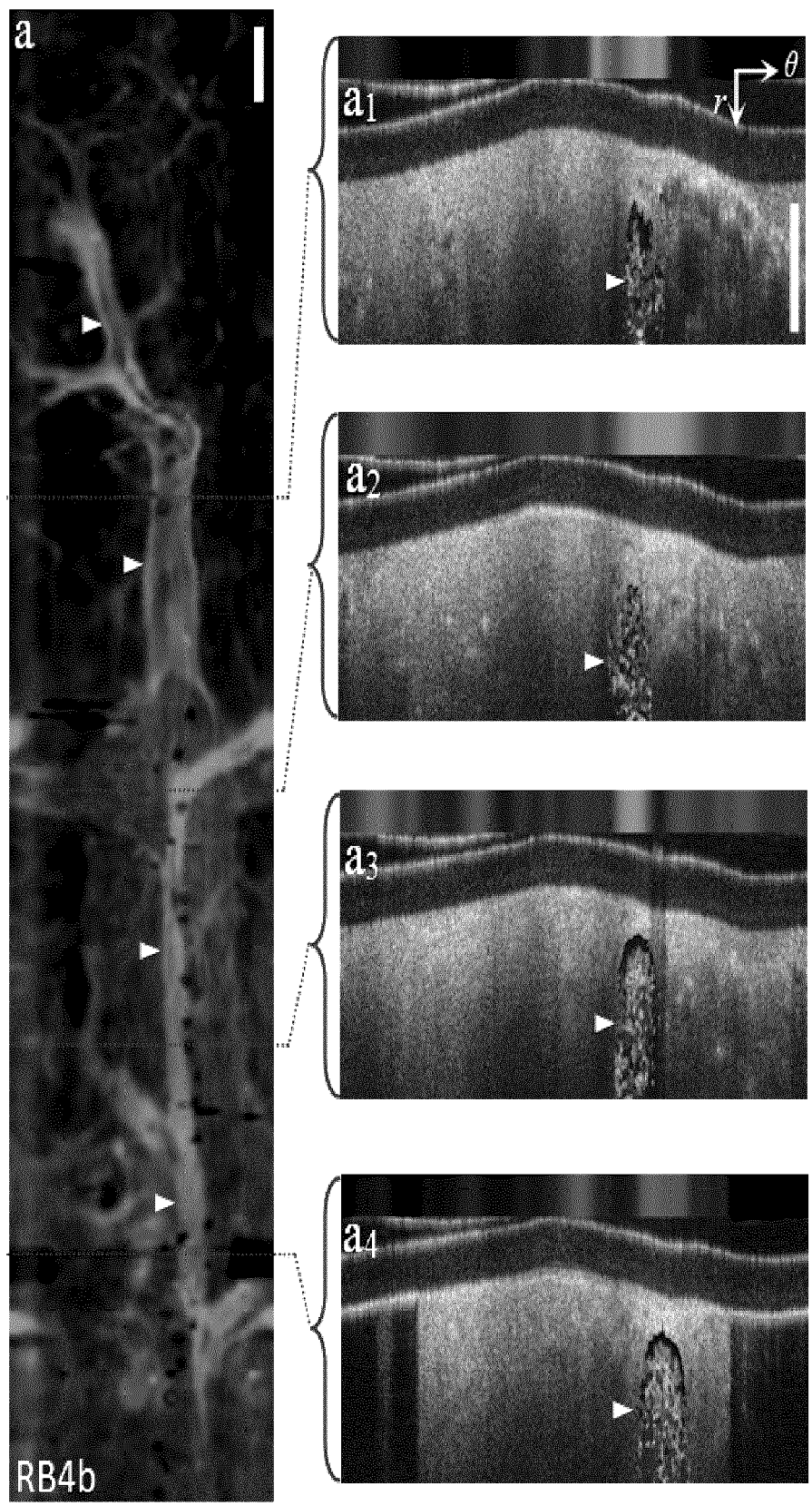
FIGS. 10A, 10B and 10C are AF and OCT images of sections of human airway in vivo.
Figure 10B:
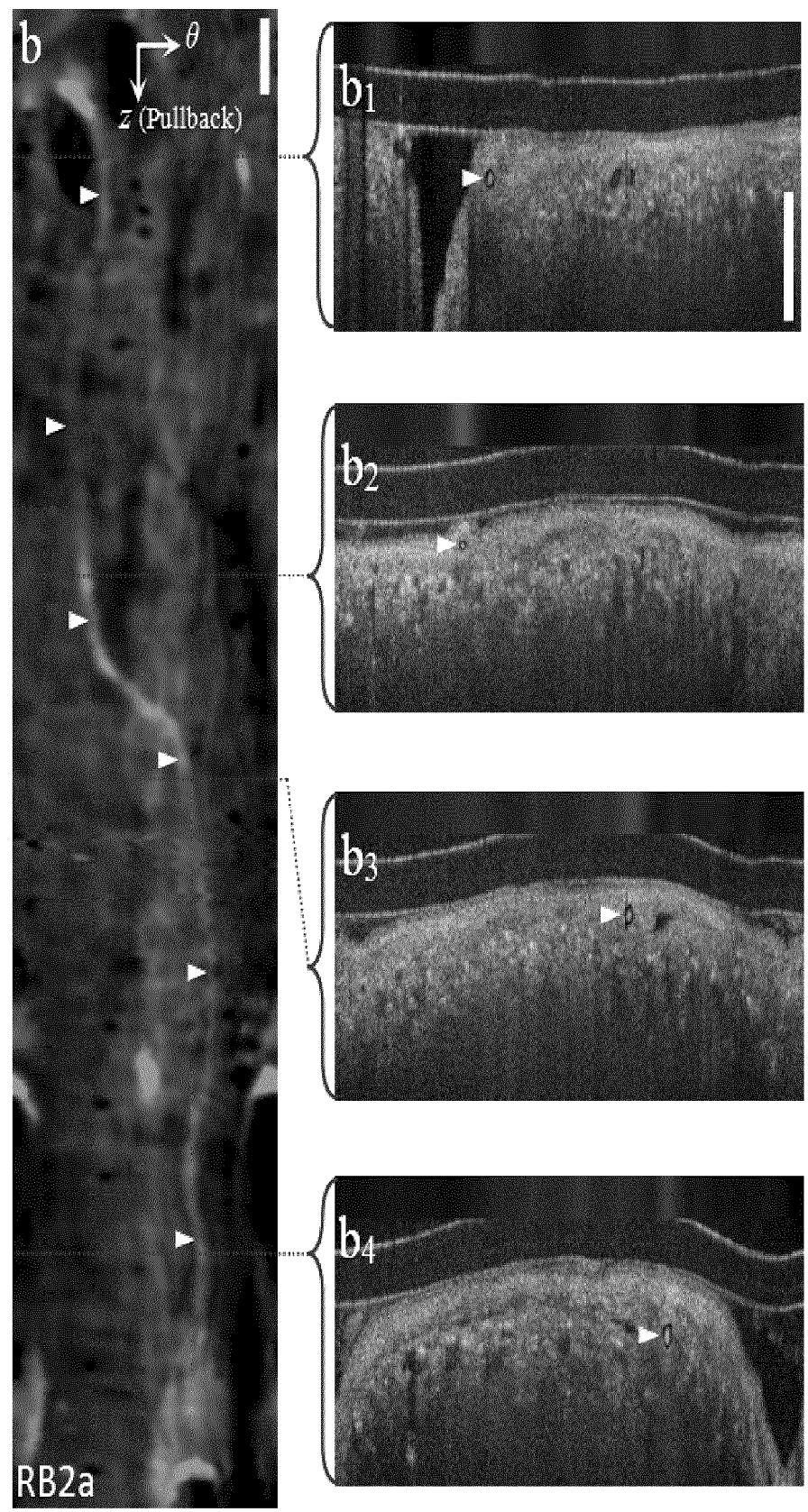
Figure 10C:
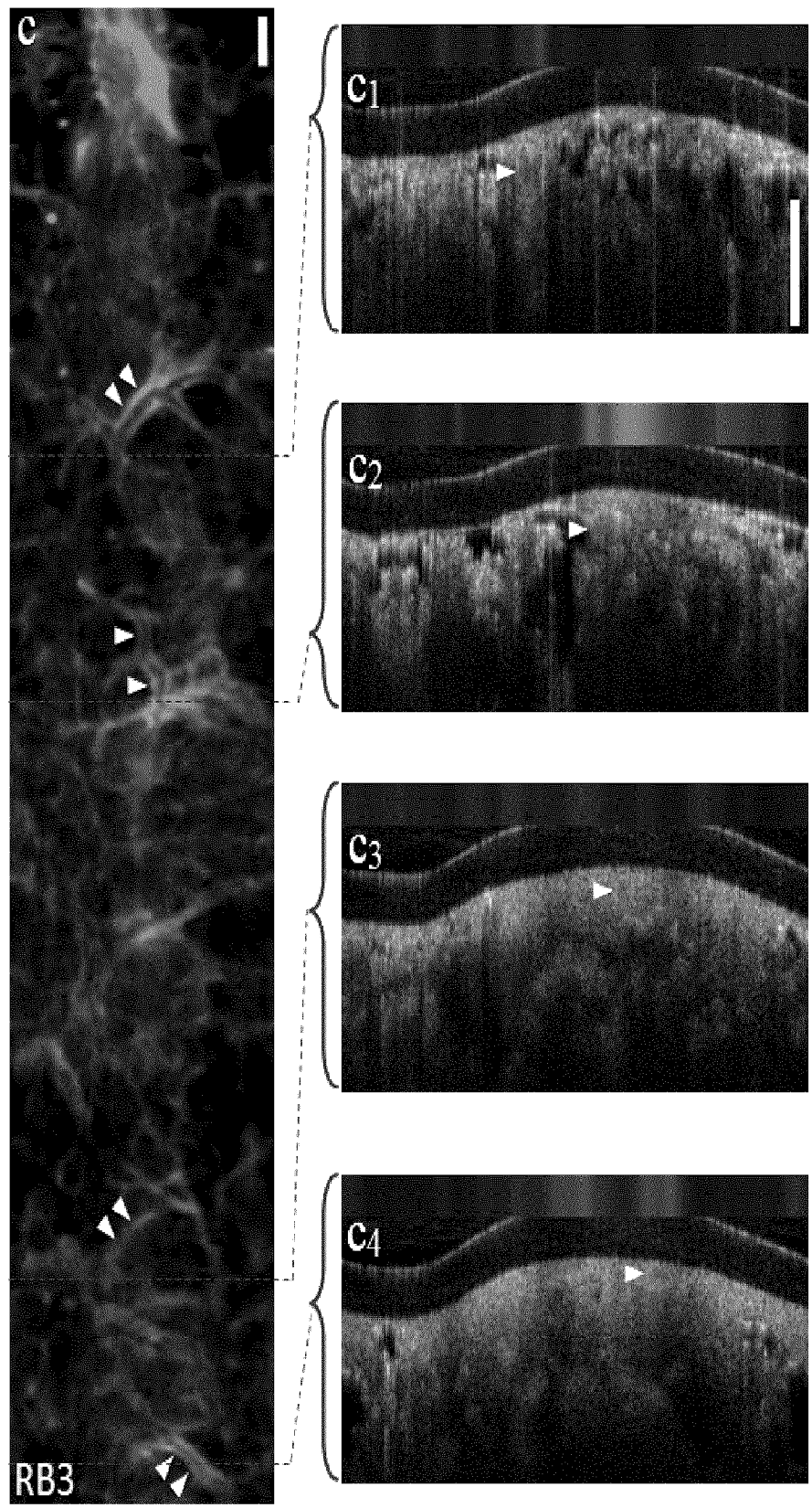

Some example images are shown in FIGS. 10A to 10C. These Figures are AF z-θ maps of three pullbacks from airway sections with high-density vasculature that demonstrate vascular network visualization by AF/DOCT: a1-4, b1-4, and c1-4 are cross-sectional AF/OCT images in the polar coordinates (r, θ) corresponding to the dashed lines shown in the three scans. In each case the white bar is 1 mm.

Vascular networks close to the airway luminal surface are clearly visualized in the AF maps. Blood vessels were also identified in the DOCT images. As illustrated FIG. 10A and FIG. 10B, the location of strong AF signals corresponding to blood vessel walls correlates well with the Doppler signals from the vessels. Also, vascular networks can be identified in the AF map even without Doppler OCT as shown in FIG. 10C. Unlike Doppler OCT that requires dense A-scans per frame and, in turn, slow rotational scans, AF imaging co-registered with OCT can visualize a vascular network with no requirement for slow scans. Therefore, performing AF/OCT scans may improve the speed of vasculature-sensitive imaging. Additionally, Doppler OCT is not sensitive to blood flow perpendicular to the excitation light, while AF imaging visualizes fibers in the vessel walls independent of the blood flow orientation with respect to the excitation light.

The prototype experiments showed that the AF and OCT datasets provide two different views into the airway wall. The wide field-of-view map of AF from the airway's luminal surface identifies potentially high-risk areas that suggest further investigation of the higher-resolution volumetric OCT data. As the AF map can be displayed in real time during pullback of the probe, a bronchoscopist can identify potentially high-risk areas in the AF map to be further investigated in the corresponding OCT scans. The combination of AF imaging followed by interpretation of co-registered OCT scans may provide valuable information about the location and pattern (invasive or non-invasive) of a tumor that can be used to guide sample collection from small peripheral nodules.

The ability of AF imaging to image vasculature, particularly in small airways can improve the safety of biopsy procedures. Tumors often have rich blood supplies. Breaking a large blood vessel while sampling a tumor may cause serious hemorrhage. By detecting large vessels near the tissue surface, AF imaging can reduce the risk of hemorrhage and resulting complications when taking biopsy samples. Unlike R-EBUS with no Doppler contrast (currently the only other imaging modality deployable in the small airways), AF/DOCT can differentiate large blood vessels from nodules (biopsy collection is required in the latter case but is risky in the former case). Results show AF/OCT has at least the same sensitivity as R-EBUS and may have better specificity than R-EBUS for detecting abnormal tissues that would benefit from further investigation.

Additional Example PS-OCT Embodiment

Figure 11:
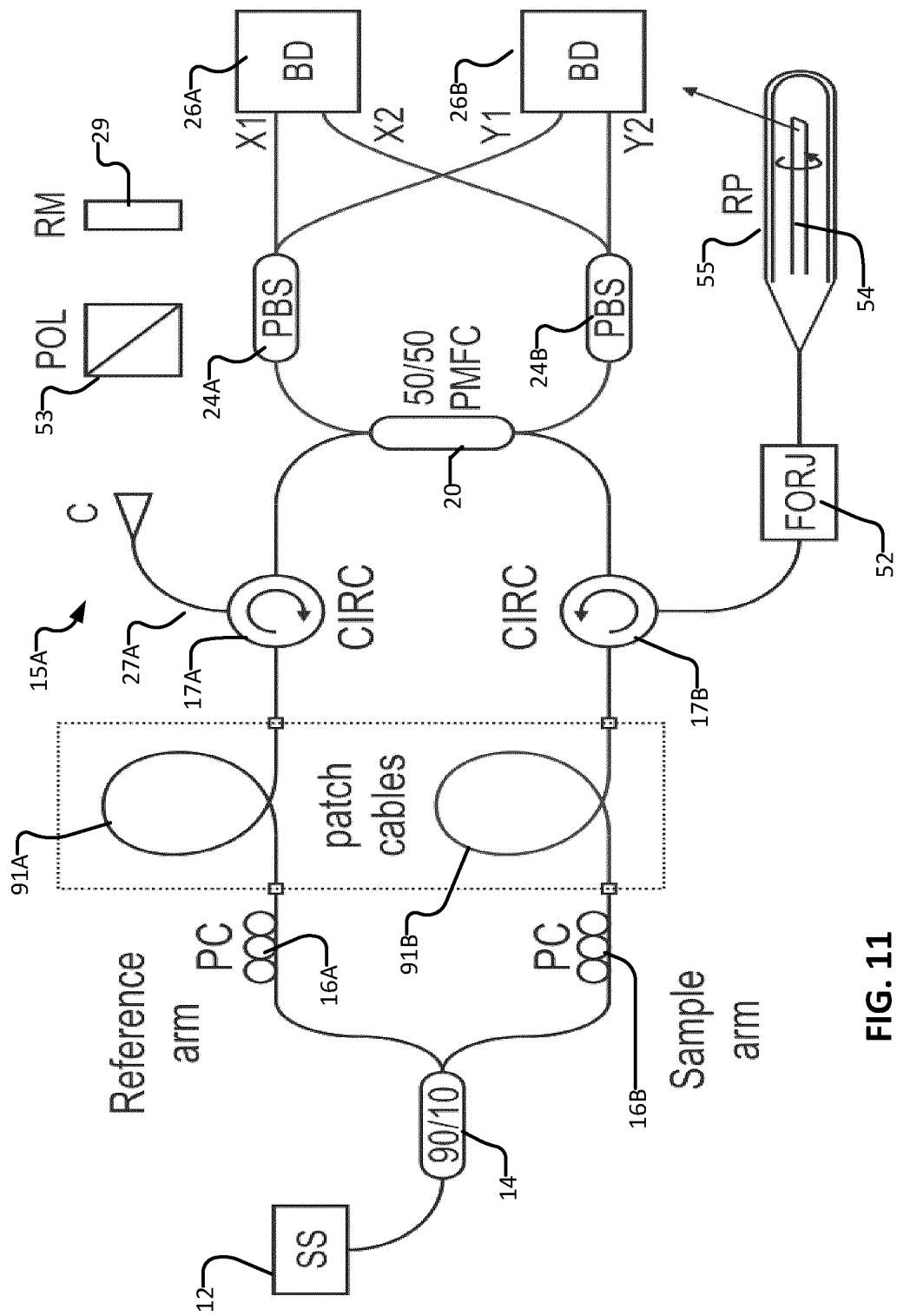
FIG. 11 is a schematic view of an example OCT imaging system according to another example embodiment.

FIG. 11 shows an OCT system 90 according to another example embodiment. Some components of system 90 that can be the same as or similar to components of other systems described herein are indicated by the same reference numbers. System 90 applies polarization diversity detection as described above. System 90 includes a single-mode (SM) optical fiber patch cord 91A and a polarization-maintaining (PM) optical fiber patch cord 91B that may be used in a polarization-sensitive OCT (PSOCT) imaging mode to facilitate depth-encoded PSOCT. Lengths of patch cords 91A and 91B may be on the order of 10 m. For example, using patch cords 91A and 91B having lengths of 12 m provides a depth separation of 2.33 mm in air (1.66 mm in tissue) between the two polarization states. Patch cords 91A and 91B may be removed and replaced with short sections of optical fiber to configure apparatus 90 for polarization-independent OCT imaging.

A polarizer 53 mounted in a rotational mount is inserted before end mirror 29 of reference arm 15A to balance the reference polarization powers at the detectors as described herein. Polarization controllers 16A and 16B allow adjustment of the laser polarization prior to entry into optical circulators 17A and 17B when the interferometer is being operated in a polarization-independent OCT imaging mode.

From the foregoing description it can be seen that the technology described herein has a number of inventive aspects that may be applied individually and in combination. Without limitation these include:

OCT systems which apply polarization diversity detection. Systems 10, 50, 80 and 90 are examples of such systems. Such systems may incorporate an optical coupler 20 connected to receive light by way of non-PM optical fibers and to transmit light to polarizing beam splitters of a polarization diversity detection system by way of PM optical fibers. Such an OCT imaging system may optionally be configured for Doppler OCT imaging.

PS-OCT systems. Systems 10, 50, 80 and 90 are examples of systems that may be configured for PS OCT imaging. A PS OCT imaging system may optionally be configured for Doppler PS OCT imaging.

Fluorescence imaging systems. The fluorescence imaging component of system 80 is a representative example. Such systems may optionally be combined with OCT systems to provide fluorescence OCT or AF-OCT imaging. In such cases the OCT imaging may optionally comprise Doppler OCT imaging. Such systems may incorporate a probe tip having a construction which includes a clad spacer such as MMF 89A of FIG. 7A.

Methods for imaging vasculature by AF imaging. Such methods are particularly suited to imaging vasculature in small airways. Such methods may apply apparatus that incorporates a probe tip having a construction which includes a clad spacer (of which MMF 89A is an illustrative example).

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

In embodiments of the invention processing of data, for example, to provide images, may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for an imaging device may implement methods as described herein by executing software instructions in a program memory accessible to the processors.

Where a component (e.g. a circulator, combiner, polarization control, processor, display, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the example embodiments set forth in the examples, but should be given the broadest interpretation consistent with the description as a whole.

REFERENCES

The following references describe various OCT and AF imaging systems as well as related components and techniques. Features described in these references may be used in combination with the systems, apparatus and methods described herein. These references are hereby incorporated herein by reference.

1. D. Huang, et al., "Optical Coherence Tomography," *Science* 245(5035), 1178-81 (1991).
2. J. G. Fujimoto, et al., "Optical biopsy and imaging using optical coherence tomography," *Nat. Med.* 1(9), 970-1 (1995).
3. G. J. Tearney, et al., "In vivo endoscopic optical biopsy with optical coherence tomography," *Science* 276 (5321), 2037-9 (1997).
4. M. R. Hee, D. Huang, E. Swanson, and J. G. Fujimoto, "Polarization-sensitive low-coherence reflectometer for birefringence characterization and ranging," *J. Opt. Am. B* 9(6), 903-908 (1992).
5. J. F. de Boer, T. E. Milner, M. J. C. Van Gernert, and J. S. Nelson, "Two-dimensional birefringence imaging in biological tissue by polarization-sensitive optical coherence tomography," *Opt. Lett.* 22(12), 934-936 (1997).
6. J. F. de Boer, S. M. Srinivas, A. Malekafzali, Z. Chen, and J. S. Nelson, "Imaging thermally damaged tissue by polarization sensitive optical coherence tomography," *Opt. Express* 3(6), 212-218 (1998).
7. M. J. Everett, K. Schoenenberger, B. W. Colston, Jr., and L. B. Da Silva, "Birefringence characterization of biological tissue by use of optical coherence tomography," *Opt. Lett.* 23(3), 228-230 (1998).
8. J. F. de Boer, T. E. Milner, and J. S. Nelson, "Determination of the depth-resolved Stokes parameters of the light backscattered from turbid media by use of the polarization-sensitive optical coherence tomography," *Opt. Lett.* 24(5), 300-302 (1999).
9. G. Yao and V. Wang, "Two-dimensional depth-resolved Muller matrix characterization of biological tissue by optical coherence tomography," *Opt. Lett.* 24(8), 537-539 (1999).
10. S. Jiao, G. Yao, L. V. Wang, "Depth-resolved two-dimensional Stokes vectors of backscattered light and Mueller matrices of biological tissue measured with optical coherence tomography," *Appl. Opt.* 39(34), 6318-6324 (2000).
11. C. K. Hitzenberger, E. Gözinger, M. Sticker, M. Pircher, and A. F. Fercher, "Measurement and imaging of birefringence and optic axis orientation by phase resolved polarization sensitive optical coherence tomography," *Opt. Express* 9(13), 780-790 (2001).
12. C. E. Saxer, J. F. de Boer, B. H. Park, Y. Zhao, Z. Chen, and J. S. Nelson, "High-speed fiber-based polarization-sensitive optical coherence tomography of in vivo human skin," *Opt. Lett.* 25(18), 1355-1357 (2000).
13. B. H. Park, C. Saxer, S. M. Srinivas, J. S. Nelson, "In vivo burn depth determination by high-speed fiber-based polarization sensitive optical coherence tomography," *J. Biomed. Opt.* 6(4), 474-479 (2001).
14. M. C. Pierce, B. H. Park, B. Cense, and J. F. de Boer, "Simultaneous intensity, birefringence, and flow measurements with high-speed fiber-based optical coherence tomography," *Opt. Lett.* 27(17), 1534-1536 (2002).
15. B. H. Park, M. C. Pierce, B. Cense, and J. F. de Boer, "Real-time multi-functional optical coherence tomography," *Opt. Express* 11(7), 782-793 (2003).
16. B. H. Park, M. C. Pierce, B. Cense, and J. F. De Boer, "Jones matrix analysis for a polarization-sensitive optical coherence tomography system using fiber-optic components," *Opt. Lett.* 29(21), 2512-2514 (2004).
17. K. H. Kim, B. H. Park, Y. Tu, T. Hasan, B. Lee, J. Li, and J. F. de Boer, "Polarization-sensitive optical frequency domain imaging based on unpolarized light," *Opt. Express* 19(2). 552-561 (2010).
18. B. Baumann, W. J. Choi, B. Potsaid, D. Huang, J. S. Duker, and J. G. Fujimoto, "Swept-source/Fourier domain polarization sensitive optical coherence tomography with a passive polarization delay unit," *Opt. Express* 20(9), 10218-10230 (2012).
19. M. Pierce, et al, "Effects of sample arm motion in the endoscopic polarization-sensitive optical coherence tomography," *Opt. Express* 13(15), 5739-5749 (2005).
20. W. Y. Oh, et al, "High-speed polarization sensitive optical frequency domain imaging with frequency multiplexing," *Opt. Express* 16(2), 1096-1103 (2008).
21. D. P. Davé, T. Akkin, and T. E. Milner, "Polarization-maintaining fiber-based optical low-coherence reflectometer for characterization and ranging of birefringence," *Opt. Lett.* 28(19), 1775-1777 (2003).
22. M. K. Al-Qaisi and T. Akkin, "Polarization-sensitive optical coherence tomography based on polarization-maintaining fibers and frequency multiplexing," *Opt. Express* 16(17), 13032-13041 (2008).
23. M. Yamanari, S. Makita, and Y. Yasuno, "Polarization-sensitive swept source optical coherence tomography with continuous source polarization modulation," *Opt. Express* 16(8), 5892-5906 (2008).
24. E. Götzinger, B. Baumann, M. Pircher, and C. K. Hitzenberger, "Polarization maintaining fiber based ultra-high resolution spectral domain polarization sensitive optical coherence tomography," *Opt. Express* 17(25), 22704-22717 (2009).
25. M. Bonesi, et al, "High-speed polarization sensitive optical coherence tomography scan engine based on Fourier domain mode locked laser," Biomed. *Opt. Express* 3(1), 2987-3000 (2012).
26. M. D. Lee, H. Pahlevaninezhad, V. X. D. Yang, S. Lam, C. MacAulay, and P. M. Lane, "Fiber-based polarization diversity detection for rotary probe optical coherence tomography," (submitted).
27. S. H. Yun, C. Boudoux, G. J. Tearney, and B. E. Bouma, "High-speed wavelength-swept semiconductor laser with a polygon-scanner-based wavelength filter", *Opt. Lett.* 28(20), 1981-1983 (2003).
28. B. E. Bouma, S. H. Yun, B. J. Vakoc, M. J. Suter, and G. J. Tearney, "Fourier-domain optical coherence tomography: recent advances toward clinical utility," *Curr. Opin. Biotechnol.* 20(1), 111-8 (2009).
29. G. J. Tearney, et al, "Scanning single-mode fiber optic catheter-endoscope for optical coherence tomography," *Opt. Lett.* 21(7), 543-545 (1996).
30. J. G. Fujimoto, S. A. Boppart, G. J. Tearney, B. E. Bouma, C. Pitris, and M. E. Brezinski, "High resolution in vivo intra-arterial imaging with optical coherence tomography," *Heart* 82(2), 128-133 (1999).
31. X. Li, C. Chudoba, T. Ko, C. Pitris, and J. G. Fujimoto, "Imaging needle for optical coherence tomography," *Opt. Lett.* 25(20), 1520-1522 (2000).
32. X. D. Li, et al, "Optical coherence tomography: advanced technology for the endoscopic imaging of Barrett's esophagus," *Endoscopy* 32(12), 921-30 (2000).
33. X. Li, T. H. Ko, and J. G. Fujimoto, "Intraluminal fiber-optic Doppler imaging catheter for structural and functional optical coherence tomography," *Opt. Lett.* 26(23), 1906-1908 (2001).
34. G. T. Bonnema, K. Cardinal, S. K. Williams, and J. K. Barton, "Aconcentric three element radial scanning optical coherence tomography endoscope," *J. Biophoton.* 2(6-7), 353-6 (2009).
35. D. Lorenser, X. Yang, R. W. Kirk, B. C. Quirk, R. A. McLaughlin, and D. D. Sampson, "Ultrathin side-viewing needle probe for optical coherence tomography," *Opt. Lett.* 36(19), 3894-3896 (2011).
36. R. Tumlinson, et al, "Endoscope-tip interferometer for ultrahigh resolution frequency domain optical coherence tomography in mouse colon," *Opt. Express* 14(5), 1878-1887 (2006).
37. J. U. Kang, J. Han, and K. Zhang, "Common-path optical coherence tomography for biomedical imaging sensing," *J. Opt. Soc. Korea* 14(1), 1-13 (2010).
38. M. Rollins and J. A. Izatt, "Optimal interferometer designs for optical coherence tomography," *Opt. Lett.* 24(21), 1484-1486 (1999).
39. M. Kobayashi, H. Hanafusa, K. Takada, and J. Noda, "Polarization-independent interferometric optical-time-domain reflectormeter," *J. Lightwave Technol.* 9(5), 623-628 (1991).
40. B. L. Heffner, W. V. Sorin, Polarization independent optical coherence-domain reflectometry, U.S. Pat. No. 5,202,745 A, filed Nov. 7, 1990, Issued Apr. 13, 1993.
41. M. C. Pierce, et al., "Effects of sample arm motion in endoscopic polarization-sensitive optical coherence tomography," *Opt. Express* 13(15), 5739-5749 (2005).
42. S. Lam, T. Kennedy, M. Unger, Y. E. Miller, D. Gelmont, V. Rusch, B. Gipe, D. Howard, J. C. LeRiche, A. Coldman, and A. F. Gazdar, "Localization of bronchial intraepithelial neoplastic lesions by fluorescence bronchoscopy", *Chest* 113(3), 696-702 (1998).
43. T. C. Kennedy, S. Lam, and F. R. Hirsch, "Review of recent advances in fluorescence bronchoscopy in early localization of central airway lung cancer", *Oncologist* 6(3), 257-62 (2001).
44. J. Hung, S. Lam, J. C. LeRiche, and B. Palcic, "Autofluorescence of normal and malignant bronchial tissue", *Surg. Med.* 11(2), 99-105(1991).
45. B. J. Venmans, H. van der Linden, T. J. van Boxem, P. E. Postmus, E. F. Smit, T. G. Sutedja, "Early detection of pre-invasive lesions in high risk patients. A comparison of conventional fiber optic and fluorescence bronchoscopy", *J. Bronchoscopy* 5(4), 280-283 (1998).
46. M. Tsuoi, A. Hayashi, N. Ikeda, H. Honda, Y. Kato, S. Ichinose, and H. Kato, "Optical coherence tomography in the diagnosis of bronchial lesions," *Lung Cancer* 49(3), 387-394 (2005).
47. S. Lam, B. Standish, C. Baldwin, A. McWilliams, J. leRiche, A. Gazdar, A. L. Vitkin, V. Yang, N. Ikeda, and C. MacAulay, "In vivo optical coherence tomography imaging of preinvasive bronchial lesions," *Clin. Cancer Res.* 14(7), 1078-0432(2008).
48. H. Pahlevaninezhad, I. Cecic, A. M. D. Lee, A. H. Kyle, S. Lam, C. MacAulay, and P. M. Lane, "Multi-modal tissue imaging: using co-registered optical tomography data to estimate tissue autofluorescence intensity change due to scattering and absorption by neoplastic epithelial cells", *J. Biomed. Opt.* 18(10), 106007 (2013).
49. J. K. Barton, F. Guzman, and A. Tumlinson, "Dual modality instrument for simultaneous optical coherence tomography imaging an fluorescence spectroscopy," *J. Biomed. Opt.* 9(3), 618-623 (2004).
50. S. Yuan, Q. Li, J. Jiang, A. Cable, and Y. Chen, "Three-dimensional coregistered optical coherence tomography and line-scanning fluorescence laminar optical tomography," *Opt. Lett.* 34(11), 1615-1617 (2009).
51. S. Yuan, C. A. Roney, J. Wierwille, C. W. Chen, B. Xu, G. Griffiths, J. Jiang, H. Ma, A. Cable, R. M. Summers, and Y. Chen, "Co-registered optical coherence tomography and fluorescence molecular imaging for simultaneous morphological and molecular imaging," *Phys. Med. Biol.* 55(1), 191-206(2010).
52. J. Park, A. J. A. Jo, S. Shrestha, P. Pande, Q. Wan, and B. E. Applegate, "A dual-modality optical coherence tomography and fluorescence lifetime imaging microscopy system for simultaneous morphological and biochemical tissue characterization," Biomed. *Opt. Express* 1(1), 2010.
53. Y. Chen, S. Yuan, J. Wirewille, R. Naphas, Q. Li, T. R. Blackwell, P. T. Winnard, Jr., V. Raman, and K. Glunde, "Integrated optical coherence tomography (OCT) and fluorescence laminar optical tomography (FLOT)," *IEEE Journal of Selected Topics* in *Quantum Electronics* 16(4), 755-766 (2010).
54. M. Gaertner, P. Cimalla, L. Knels, S. Meissner, C. Schnabel, W. M. Kubler, and E. Koch, "Investigation of alveolar tissue deformations using OCT combined with fluorescence microscopy," *Proc. SPIE* 8091, Optical Coherence Tomography and Coherence Techniques V, 80911P (2011).
55. J. Y. Qu, Z. Huang, and J. Hua, "Excitation-and-collection geometry insensitive fluorescence imaging of tissue-simulating turbid media," *Appl. Opt.* 39(19), 3344-56 (2000).
56. R. J. McNichols, A. Gowda, B. A. Bell, R. M. Johnigan, K. H. Calhoun, and M. Motamedi, "Development of an endoscopic fluorescence image guided OCT probe for oral cancer detection," *Proc. SPIE* 4254, 23-30 (2001).
57. Y. T. Pan, T. Q. Xie, C. W. Du, S. Bastacky, S. Meyers, and M. L. Zeidel, "Enhancing early bladder cancer detection with fluorescence-guided endoscopic optical coherence tomography," *Opt. Lett.* 28(24), 2485-2487 (2003).
58. A. R. Tumlinson, L. P. Hariri, U. Utzinger, and J. K. Barton, "A miniature endoscope for simultaneous OCT-LIF measurement," *Appl. Opt.* 43(1), 113-121 (2004).
59. L. P. Hariri, A. R. Tumlinson, D. G. Besselsen, U. Utzinger, and J. K. Barton, "Endoscopic optical coherence tomography and laser-induced fluorescence spectroscopy in a murine colon cancer model," *Lasers Surg. Med.* 38(4), 305-13 (2006).
60. R. A. Wall, G. T. Bonnema, and J. K. Barton, "Novel focused OCT-LIF endoscope," *Biomed. Opt. Express* 2(3), 421-430 (2011).
61. A. M. Winkler, P. F. Rice, J. Weichsel, J. M. Watson, M. V. Backer, J. K. Barton, "In vivo, dual-modality OCT/LIF imaging using a novel VEGF receptor-targeted NIR fluorescent probe in the AOM-treated mouse model," *Mol. Imaging Boil.* 13(6), 1173-82 (2011).
62. M. Fard, P. Vacas-Jacques, E. Hamidi, H. Wang, R. W. Carruth, J. A. Gardecki, and G. J. Tearney, "Optical coherence tomography—near infrared spectroscopy system and catheter for intravascular imaging," *Opt. Express* 21(25), 30849-30858 (2013).
63. S. Tang, T. B. Krasieva, Z. Chen, and B. J. Tromberg, "Combined multiphoton microscopy and optical coherence tomography using a 12-fs broadband source," *J. Biomed. Opt.* 11(2), 020502 (2006).
64. A. R. Tumlinson, J. K. Barton, B. Považay, H. Sattman, A. Unterhuber, R. A. Leitgeb, and W. Drexler, "Endoscopic-tip interferometer for ultrahigh resolution frequency domain optical coherence tomography in mouse colon," *Opt. Express* 14(5), 1878-1887 (2006).
65. M. T. Myaing, D. J. MacDonald, and X. Li, "Fiber-optic scanning two-photon fluorescence endoscope," *Opt. Lett.* 31(8), 1076-1078 (2006).
66. S. Tang, W. Jung, D. McCormick, T. Xie, J. Su, Y. C. Ahn, B. J. Tromberg, and Z. Chen, "Design and implementation of fiber-based multiphoton endoscopy with microelectromechanical systems scanning," *J Biomed. Opt.* 14(3), 034005 (2009).
67. S. Tang, Y. Zhou, K. K. H. Chan, and T. Lai, "Multiscale multimodal imaging with multiphoton microscopy and optical coherence tomography," *Opt. Lett.* 36(24), 4800-4802 (2011).
68. G. Liu and Z. Chen, "Fiber-based combined optical coherence and multiphoton endomicroscopy," *J. Biomed. Opt.* 16(3), 036010 (2011).
69. K. Murari, Y. Zhang, S. Li, Y. Chen, M. J. Li, and X. Li, "Compensation-free, all-fiber-optc, two-photon endomicroscopy at 1.55 μm," *Opt. Lett.* 36(7), 1299-1301 (2011).
70. Dai, X. Liu, and S. Jiao, "Simultaneous optical coherence tomography and autofluorescence microscopy with a single light source," *J. Biomed. Opt.* 17(8), 080502 (2012).
71. S. Y. Ryu, H. Y. Choi, J. Na, E. S. Choi, and B. H. Lee, "Combined system of optical coherence tomography and fluorescence spectroscopy based on double-cladding fiber," *Opt. Lett.* 33(20), 2347-2349 (2008).
72. H. Bao, S. Y. Ryu, B. H. Lee, W. Tao, M. Gu, "Nonlinear endomicroscopy using a double-clad fiber coupler," *Opt. Lett.* 35(7), 995-997 (2010).
73. S. Lemire-Renaud, M. Rivard, M. Strupler, D. Morneau, F. Verpillat, X. Daxhelet, N. Godbout, and C. Boudoux, "Double-clad fiber coupler for endoscopy", *Opt. Express* 18(10), 9755-9764 (2010).
74. S. Liang, A. Saidi, J. Jing, G. Liu, J. Li, J. Zhang, C. Sun, J. Narula, Z. Chen, "Intravascular atherosclerotic imaging with combined fluorescence and optical coherence tomography probe based on a double-clad fiber combiner," *J. Biomed. Opt.* 17(7), 070501 (2012).
75. J. Mavadia, J. Xi, Y. Chen, and X. Li, "An all-fiber-optic endoscopy platform for simultaneous OCT and fluorescence imaging," *Biomed. Express* 3(11), 2851-2859 (2012).
76. Yelin, B. E, Bouma, S. H. Yun, and G. J. Tearney, "Double-clad fiber for endoscopy," *Opt. Lett.* 29(20), 2408-2410 (2004).
77. L. Wang, H. Y. Choi, Y. Jung, B. H. Lee, and K. T. Kim, "Optical probe based on double-clad optical fiber for fluorescence spectroscopy," *Opt. Express* 15(26), 17681-17689 (2007). Lorenser, B. C. Quirk, M. Auger, W. J. Madore, R. W. Kirk, N. Godbout, D. D. Sampson, C. Boudoux, and R. A. McLaughlin, "Dual-modality needle probe for combined fluorescence imaging and three-dimensional optical coherence tomography," *Opt. Lett.* 38(3), 266-268 (2013).
78. Lee, A. M. D., et al., In vivo lung microvasculature visualized in three dimensions using fiber-optic color Doppler optical coherence tomography. J Biomed Opt, 2013. 18(5).
79. U.S. Pat. No. 5,459,570.
80. U.S. Pat. No. 5,748,598.
81. U.S. Pat. No. 5,784,352.
82. U.S. Pat. No. 6,134,003.
83. U.S. Pat. No. 6,445,939.
84. U.S. Pat. No. 6,501,551.
85. U.S. Pat. No. 6,564,087.
86. U.S. Pat. No. 6,564,089.
87. U.S. Pat. No. 6,615,072.
88. U.S. Pat. No. 6,831,781.
89. U.S. Pat. No. 6,904,199.
90. U.S. Pat. No. 7,102,756.
91. U.S. Pat. No. 7,261,687.
92. U.S. Pat. No. 7,362,444.
93. U.S. Pat. No. 7,362,500.
94. U.S. Pat. No. 7,364,543.
95. U.S. Pat. No. 7,366,376.
96. U.S. Pat. No. 7,382,949.
97. U.S. Pat. No. 7,447,408.
98. U.S. Pat. No. 7,576,865.
99. U.S. Pat. No. 7,705,992.
100. U.S. Pat. No. 7,809,225.
101. U.S. Pat. No. 7,809,226.
102. U.S. Pat. No. 7,813,609.
103. U.S. Pat. No. 7,925,133.
104. U.S. Pat. No. 7,929,148.
105. U.S. Pat. No. 7,952,718.

106. U.S. Pat. No. 8,369,669.
107. U.S. Pat. No. 8,503,844.
108. U.S. Pat. No. 8,676,013.
109. U.S. Pat. No. 8,712,506.
110. U.S. Pat. No. 8,792,757.
111. U.S. Pat. No. 8,903,475.
112. U.S. Pat. No. RE43875.
113. US Patent application 20060158655.
114. US Patent application 20080097224.
115. US patent application 20080252900.
116. US patent application 20130023760.
117. US patent application 20130331689.
118. US patent application 20140275986.
119. US patent application 20140276108
120. US patent application 20140309527.
121. PCT international patent application WO9732182.
122. European patent 1804638.
123. European patent 2412298.
124. European patent application 2278267.
125. European patent application 2659852.
126. European patent application 2677272.

What is claimed is:

1. Apparatus for optical coherence tomography comprising:
    a reference arm;
    a sample arm,
    a light splitter connected to direct a first portion of light from a light source into the reference arm by way of a first non-polarization-maintaining optical fiber path and a second portion of light from the light source into the sample arm by way of a second non-polarization-maintaining optical fiber path,
    a light combiner connected to receive light from the reference arm by way of a third non-polarization-maintaining optical fiber path and to receive light from the sample arm by way of a fourth non-polarization-maintaining optical fiber path, the light combiner configured to allow interference of the light received from the sample and reference arms,
    the light combiner having first and second outputs respectively connected to first and second polarizing beam splitters by first and second polarization maintaining optical fiber paths, the first and second polarizing beam splitters each having first and second outputs, the first outputs of the first and second polarizing beam splitters connected by optical fibers to deliver light having a first state of polarization to a first light detector, the second outputs of the first and second polarizing beam splitters connected by optical fibers to deliver light having a second state of polarization distinct from the first state of polarization to a second light detector.

2. Apparatus according to claim 1 wherein the light combiner comprises first and second input ports configured to receive single mode optical fibers and first and second output ports configured to receive polarization maintaining optical fibers.

3. Apparatus according to claim 2 wherein the light combiner comprises first and second dual fiber collimators arranged to provide collimated beams that intersect at a non-polarizing beamsplitter, wherein first sides of the first and second dual fiber collimators are respectively connected to the first and second input ports and second sides of the first and second dual fiber collimators are respectively connected to the first and second output ports.

4. Apparatus according to claim 3 wherein the non-polarizing beamsplitter is a 50/50 beamsplitter.

5. Apparatus according to claim 2 wherein the first and second output ports are each configured to non-rotationally engage the polarization maintaining optical fiber.

6. Apparatus according to claim 1 wherein the light combiner comprises a 50/50 light combiner.

7. Apparatus according to claim 1 comprising a first light circulator connected to the first and third non-polarization-maintaining optical fiber paths, the first light circulator configured to direct light from the first non-polarization-maintaining optical fiber paths into a non-polarization-maintaining optical fiber path of the reference arm and to direct light from the non-polarization-maintaining optical fiber path of the reference arm into the third non-polarization-maintaining optical fiber path.

8. Apparatus according to claim 7 comprising a second light circulator connected to the second and fourth non-polarization-maintaining optical fiber paths, the second light circulator configured to direct light from the second non-polarization-maintaining optical fiber paths into a non-polarization-maintaining optical fiber path of the sample arm and to direct light from the non-polarization-maintaining optical fiber path of the sample arm into the fourth non-polarization-maintaining optical fiber path.

9. Apparatus according to claim 1 wherein the light splitter is configured so that the second portion of light directed into the sample arm is significantly greater in power than the first portion of light directed into the reference arm.

10. Apparatus according to claim 1 comprising a processor connected to process signals from the first and second light detectors to determine a retardation of the sample.

11. Apparatus according to claim 10 wherein determining the tangent of the retardation comprises dividing amplitudes of the signals detected at the first and second light detectors.

12. Apparatus according to claim 10 wherein the processor is further configured to determine polarization independent structural information and the processing comprises computing a sum of squares of amplitudes of the signals detected at the first and second light detectors.

13. Apparatus according to claim 10 wherein the processing comprises determining a root mean square of amplitudes of the signals detected at the first and second light detectors.

14. Apparatus according to claim 1 wherein the sample arm comprises a fiber optic rotary joint, probe assembly comprising an optical fiber having a probe tip at a distal end thereof and a drive system coupled to rotate the optical fiber.

15. Apparatus according to claim 14 wherein the fiber optic rotary joint comprises an input port, a first lens arranged to collimate light entering the input port, a second lens arranged to couple light collimated by the first lens into the optical fiber of the probe assembly and a dichroic mirror between the first and second lenses, the dichroic mirror constructed to pass light having wavelengths emitted by the light source and to reflect light of other wavelengths.

16. Apparatus according to claim 15 comprising a second light source operable to emit fluorescence excitation light, the second light source arranged to direct the fluorescence excitation light onto the dichroic mirror.

17. Apparatus according to claim 14 wherein the probe tip comprises a focusing element arranged to direct light onto a light deflector and a section of clad fiber between the focusing element and the optical fiber of the probe.

18. Apparatus according to claim 17 wherein the section of clad fiber comprises a section of step-index multimode fiber.

19. Apparatus according to claim 18 wherein the optical fiber of the probe comprises a dual clad fiber.

20. Apparatus according to claim 19 wherein the focusing element comprises a graded index optical fiber having a core diameter $D_{GRIN}$ and a length of the section of clad fiber satisfies:

$$L_{MMF} \times \frac{2\lambda_{OCT}}{\pi w_{OCT} n_{OCT}} < D_{GRIN},$$

where $w_{OCT}$, and $n_{OCT}$ are the half of the mode field diameter of the core of the dual clad fiber and refractive index of a core of the clad fiber at the wavelength $\lambda_{OCT}$ of the light source.

21. Apparatus according to claim 20 wherein a diameter $D_{MMF}$ of the core of the multimode fiber is given by:

$$D_{MMF} > L_{MMF} \times \frac{2\lambda_{OCT}}{\pi w_{OCT} n_{OCT}}.$$

22. Apparatus according to claim 1 wherein the light source comprises a wavelength-swept laser emitting near infrared wavelengths in the range of 850 nm to 2000 nm.

23. Apparatus according to claim 1 wherein the optical fibers connecting the outputs of the first and second polarizing beam splitters to the first and second light detectors comprise polarization maintaining optical fibers.

* * * * *